US012724032B2

(12) United States Patent
Reategui et al.

(10) Patent No.: US 12,724,032 B2
(45) Date of Patent: Sep. 1, 2026

(54) HIGHLY SENSITIVE PLATFORM TO CHARACTERIZE EXTRACELLULAR VESICULAR BIOMARKERS FOR CANCER IMMUNOTHERAPY

(71) Applicants: OHIO STATE INNOVATION FOUNDATION, Columbus, OH (US); SPOT BIOSYSTEMS LTD., Columbus, OH (US)

(72) Inventors: Eduardo Reategui, Columbus, OH (US); Thi Hien Luong Nguyen, Columbus, OH (US); Kwang Joo Kwak, Columbus, OH (US); L. James Lee, Columbus, OH (US)

(73) Assignee: OHIO STATE INNOVATION FOUNDATION and SPOT BIOSYSTEMS LTD., Columbus, OH (US)

( * ) Notice: Subject to any disclaimer, the term of this patent is extended or adjusted under 35 U.S.C. 154(b) by 684 days.

(21) Appl. No.: 18/021,365

(22) PCT Filed: Aug. 18, 2021

(86) PCT No.: PCT/US2021/046561

§ 371 (c)(1),
(2) Date: Feb. 14, 2023

(87) PCT Pub. No.: WO2022/040350

PCT Pub. Date: Feb. 24, 2022

(65) Prior Publication Data

US 2023/0341407 A1 Oct. 26, 2023

Related U.S. Application Data

(60) Provisional application No. 63/067,531, filed on Aug. 19, 2020.

(51) Int. Cl.
*G01N 33/575* (2026.01)
*G01N 33/53* (2006.01)
*G01N 33/543* (2006.01)

(52) U.S. Cl.
CPC ... *G01N 33/57585* (2026.01); *G01N 33/5308* (2013.01); *G01N 33/54386* (2013.01); *G01N 2333/70596* (2013.01)

(58) Field of Classification Search
None
See application file for complete search history.

(56) References Cited

U.S. PATENT DOCUMENTS

| | | | | |
|---|---|---|---|---|
| 6,812,023 | B1 | 11/2004 | Lamparski et al. | |
| 10,669,535 | B2 | 6/2020 | Pendergrast et al. | |
| 2008/0213814 | A1* | 9/2008 | Gerion | C12Q 1/001 435/287.9 |
| 2013/0220412 | A1* | 8/2013 | Hatton | H10K 30/82 438/82 |
| 2015/0111308 | A1 | 4/2015 | Yu et al. | |
| 2016/0202248 | A1* | 7/2016 | Lee | G01N 33/531 506/9 |
| 2017/0328904 | A1 | 11/2017 | Lee et al. | |
| 2018/0179577 | A1 | 6/2018 | Hu et al. | |
| 2018/0216170 | A1 | 8/2018 | Lee et al. | |
| 2019/0049438 | A1 | 2/2019 | Liu et al. | |
| 2019/0078159 | A1 | 3/2019 | Wong et al. | |
| 2019/0093105 | A1 | 3/2019 | Gibbings et al. | |
| 2020/0057068 | A1 | 2/2020 | Lobb et al. | |
| 2020/0085401 | A1 | 3/2020 | Hamada et al. | |
| 2020/0179531 | A1 | 6/2020 | Hawthorne et al. | |
| 2020/0191778 | A1 | 6/2020 | Huang et al. | |

FOREIGN PATENT DOCUMENTS

| | | | | |
|---|---|---|---|---|
| CN | 110791504 | A | 2/2020 | |
| CN | 111537725 | A | 8/2020 | |
| EP | 3327440 | A1 | 5/2018 | |
| WO | WO2017/198695 | A1 | 11/2017 | |
| WO | WO-2018046736 | A1 * | 3/2018 | G01N 33/5743 |
| WO | 2018/129481 | A2 | 7/2018 | |
| WO | WO2019/094692 | A2 | 5/2019 | |
| WO | WO-2019140305 | A1 * | 7/2019 | G01N 33/6803 |
| WO | WO2020/160402 | A1 | 8/2020 | |

(Continued)

OTHER PUBLICATIONS

Kim et al., Exosomal PD-L1 promotes tumor growth through immune escape in non-small cell lung cancer, Experimental & Molecular Medicine, 51(94), (2019), (13 pages). (Year: 2019).*

(Continued)

*Primary Examiner* — Ellen J Marcsisin
(74) *Attorney, Agent, or Firm* — MICHAEL BEST & FRIEDRICH LLP

(57) ABSTRACT

Methods and systems for characterizing extracellular vesicular biomarkers using a biochip with gold nanoparticles. The biochip includes a glass surface, a gold film layer on the glass surface, a plurality of gold nanoparticles coupled to the gold film layer, and a plurality of biotinylated antibodies coupled to the gold nanoparticles. In some implementations, the gold film layer of the biochip is coated with polyethylene glycol (PEG). The biotinylated antibodies are selected to capture specific types of extracellular vesicles. PD-L1/PD-1 proteins and RNAs in extracellular vesicles were characterized for cancer immunotherapy.

8 Claims, 21 Drawing Sheets

(56) References Cited

FOREIGN PATENT DOCUMENTS

WO 2021/128678 A1 7/2021

OTHER PUBLICATIONS

Lee et al., Application of Gold Nanoparticle to Plasmonic Biosensors, Int. J. Mol. Sci., 19, (2018), 14 pages. (Year: 2018).*
Kandimalla, Vamsi K., "Influence of metal nanoparticles on fluorescence properties" (2010). Master's Theses and Doctoral Dissertations. (80 pages). http://commons.emich.edu/theses/371. (Year: 2010).*
Jakobsen et al., Exosomal proteins as potential diagnostic markers in advanced non-small cell lung carcinoma, Journal of Extracellular Vesicles, 4, (2015), 10 pages. (Year: 2015).*
Monroy-Contreras et al., Molecular Beacons: Powerful Tools for Imaging RNA in Living Cells, J. Nucleic Acids, Article ID 741723, (2011), 15 pages. (Year: 2011).*
Konoshenko et al., "Isolation of Extracellular Vesicles: General Methodologies and Latest Trends," BioMed Research International, vol. 2018, pp. 1-27. (Year: 2018).
Anonymous, "Tangential Flow Filtration Technology," Millipore Technical Brief, downloaded from: chrome-extension://efaidnbmnnnibpcajpcglclefindmkaj/https://www.sigmaaldrich.com/deepweb/assets/sigmaald rich/product/documents/395/150/tff-tn1828en-ms.pdf on Apr. 17, 2025, pp. 1-3. (Year: 2018).
Harting et al., "Inflammation-Stimulated Mesenchymal Stromal Cell-Derived Extracellular Vesicles Attenuate Inflammation," Stem Cells, 2017, 36(1): 79-90.
Elsharkawi et al., "Urine and Serum Exosomes as Novel Biomarkers in Detection of Bladder Cancer," Asian Pacific Journal of Cancer Prevention, 2019, 20(7): 2219-2224.
United States Patent Office Action for U.S. Appl. No. 17/778,765 dated Jul. 9, 2025 (12 pages).
Martin-Gracia et al., "Nanoparticle-based biosensors for detection of extracellular vesicles in liquid biopsies," J Mater Chem B, 2020, 8(31): 6710-6738.
Ermini et al., "Peptide Functionalization of Gold Nanoparticles for the Detection of Carcinoembryonic Antigen in Blood Plasma via SPR-Based Biosensor," Front Chem, 2019, 7: 40.
Qu et al., "Electrochemical Synthesis of Gold Nanoparticles in Polypyrrole for Antibody Immobilization," Proceedings of the 2009 4th IEEE International Conference on Nano/Micro Engineered and Molecular Systems, Jan. 5-8, 2009, Shenzhen, China, pp. 597-600.
Beiderman et al., "Development of local surface plasmon resonance sensor using gold nanoparticles," Nanoscale Imaging, Sensing, and Actuation for Biomedical Applications XVI, 2019, vol. 10891, 8 pages.
Nguyen et al., "An immunogold single extracellular vesicular RNA and protein (Au SERP) biochip to predict responses to immunotherapy in non-small cell lung cancer patients," J Extracell Vesicles, 2022, 11(9): e12258.
European Patent Office Partial Supplementary Search Report for Application No. 21859087.5 dated Jul. 1, 2024 (18 pages).
European Patent Office Extended Search Report for Application No. 21859087.5 dated Sep. 23, 2024 (16 pages).
Abiko et al., "IFN-gamma from lymphocytes induces PD-L1 expression and promotes progression of ovarian cancer," Br J Cancer, 2015, 112: 1501-1509.
Abramowicz et al., "Proteomic analysis of exosomal cargo: The challenge of high purity vesicle isolation," Mol. Biosyst., 2016, 12: 1407-1419.
Aguiar Jr. et al., "The effect of PD-L1 testing on the cost-effectiveness and economic impact of immune checkpoint inhibitors for the second-line treatment of NSCLC," Ann Oneal, 2017, 28: 2256-2263.
Alix-Panabières et al., "Clinical prospects of liquid biopsies," Nat. Biomed. Eng., 2017, 1: 0065.
Almehmadi et al., "Surface Enhanced Raman Spectroscopy for Single Molecule Protein Detection," Sci Rep, 2019, 9: 12356.
Ancevski Hunter et al., "PD-L1 Testing in Guiding Patient Selection for PD-1/PD-L1 Inhibitor Therapy in Lung Cancer," Mol Diagn Ther, 2018, 22: 1-10.
Andreu et al., "Tetraspanins in Extracellular Vesicle Formation and Function," Frontiers in Immunology, 2014, 5: 442.
Avgeris et al., "Circulating exosomal miRNAs: clinical significance in human cancers," Expert Review of Molecular Diagnostics, 2019, 19: 979-995.
Axelrod, "Chapter 7: Total internal reflection fluorescence microscopy," Methods Cell Biol 2008, 89: 169-221.
Bedford et al., "Surface plasmon resonance biosensors incorporating gold nanoparticles," Macromol Biosci, 2012, 12: 724-739.
Bordanaba-Florit et al., Using single-vesicle technologies to unravel the heterogeneity of extracellular vesicles. Nature Protocols, 2021, 16: 3163-3185.
Brock et al., "Liquid biopsy for cancer screening, patient stratification and monitoring," Transl Cancer Res, 2015, 4(3): 280-290.
Bruzas et al., "Advances in surface-enhanced Raman spectroscopy (SERS) substrates for lipid and protein characterization: sensing and beyond," Analyst, 2018, 143: 3990-4008.
Burr et al., "CMTM6 maintains the expression of PD-LI and regulates anti-tumour immunity," Nature, 2017, 549: 101-105.
Buschmann et al., "Evaluation of serum extracellular vesicle isolation methods for profiling miRNAs by next-generation sequencing," J. Extracell. Vesicles, 2018, 7: 1481321.
Busher, "Serum Albumin and Globulin," Clinical Methods: The History, Physical, and Laboratory Examinations, 1990, Chapter 101, pp. 497-499.
Caby et al., "Exosomal-like vesicles are present in human blood plasma," Int Immunol, 2005, 17(7): 879-887.
Cai et al., "A brief review on the mechanisms of miRNA regulation," Genomics Proteomics & Bioinformatics, 2009, 7(4): 147-154.
Camidge et al., "Comparing and contrasting predictive biomarkers for immunotherapy and targeted therapy of NSCLC," Nat Rev Clin Oneal, 2019, 16: 341-355.
Caradec et al., "Reproducibility and efficiency of serum-derived exosome extraction methods," Clin. Biochem., 2014, 47(13-14): 1286-92.
Chen et al., "Exosomal PD-L1 contributes to immunosuppression and is associated with anti-PD-1 response," Nature, 2018, 560: 382-386.
Chernyshev et al., "Size and shape characterization of hydrated and desiccated exosomes," Anal. Bioanal. Chem., 2015, 407(12): 3285-301.
Cheruvanky et al., "Rapid isolation of urinary exosomal biomarkers using a nanomembrane ultrafiltration concentrator," Am. J. Physiol. Physiol., 2007, 292: F1657-F1661.
Choi et al., "Sensitivity Enhancement by Au Nanoparticles in Surface Plasmon Resonance Chemical Sensors," Journal of Nanoscience and Nanotechnology, 2008, 8: 4569-4573.
Clancy et al., "An ARF6-Exportin-5 axis delivers pre-miRNA cargo to tumour microvesicles," Nature Cell Biology, 2019, 21: 856-866.
Cocucci et al., "Shedding microvesicles: artefacts no more," Trends in Cell Biology, 2009, 19: 43-51.
Conigliaro et al., "Exosome-mediated signaling in epithelial to mesenchymal transition and tumor progression," 2019, 8: 26.
Coumans et al., "Bulk immunoassays for analysis of extracellular vesicles," Platelets, 2017, 28: 242-248.
Cumba Garcia et al., "Isolation and Analysis of Plasma-Derived Exosomes in Patients With Glioma," Front Oneal, 2019, 9: 651.
Daaboul et al., "Digital Detection of Exosomes by Interferometric Imaging," Scientific Reports, 2016, 6: 37246.
Daassi et al., "The importance of exosomal PDLI in tumour immune evasion," Nat Rev Immunol, 2020, 20: 209-215.
Das et al., "The Extracellular RNA Communication Consortium: Establishing Foundational Knowledge and Technologies for Extracellular RNA Research," Cell, 2019, 177: 231-242.
De Toro et al., "Emerging roles of exosomes in normal and pathological conditions: New insights for diagnosis and therapeutic applications," Frontiers in Immunology, 2015, 6: 203.

(56) References Cited

OTHER PUBLICATIONS

Dear et al., "Urinary exosomes: A reservoir for biomarker discovery and potential mediators of intrarenal signalling," Proteomics, 2013, 13: 1572-1580.
Del Re M et al., "PD-L1 mRNA expression in plasma-derived exosomes is associated with response to anti-PD-1 antibodies in melanoma and NSCLC," British Journal of Cancer, 2018, 118: 820.
Diskin et al., "PD-L1 engagement on T cells promotes self-tolerance and suppression of neighboring macrophages and effector T cells in cancer," Nat Immunol, 2020, 21: 442-454.
Dong et al., "Integrated analysis of mutations, miRNA and mRNA expression in glioblastoma," BMC Systems Biology, 2010, 4: Article No. 163.
EL Andaloussi et al., "Extracellular vesicles: biology and emerging therapeutic opportunities," Nat Rev Drug Discov, 2013, 12: 347-357.
Emelyanov et al., "Cryo-electron microscopy of extracellular vesicles from cerebrospinal fluid," PloS one, 2020, 15: e0227949.
Faget et al., "Tyramide Signal Amplification for Immunofluorescent Enhancement," Methods Mol Biol, 2015, 1318: 161-72.
Fan et al., "Circulating microRNAs predict the response to anti-PD-1 therapy in non-small cell lung cancer," Genomics, 2020, 112: 2063-2071.
Fan et al., "Enhanced Sensitivity for Detection of HIV-1 p24 Antigen by a Novel Nuclease—Linked Fluorescence Oligonucleotide Assay," PloS one, 2015, 10: e0125701.
Fang, "Total internal reflection fluorescence quantification of receptor pharmacology," Biosensors (Basel), 2015, 5: 223-240.
Filipazzi et al., "Recent advances on the role of tumor exosomes in immunosuppression and disease progression," Semin Cancer Biol, 2012, 22: 342-349.
Fraser et al., "Characterization of single microvesicles in plasma from glioblastoma patients," Neuro Oncol, 2019, 21: 606-615.
Furi et al., "Extracellular vesicle isolation: present and future," Ann Transl Med, 2017, 5: 3-5.
Gámez-Valero et al., "Size-Exclusion Chromatography-Based Isolation Minimally Alters Extracellular Vesicles' Characteristics Compared to Precipitating Agents," Sci. Rep., 2016, 6: 33641.
Garon et al., "Pembrolizumab for the treatment of non-small-cell lung cancer," New England Journal of Medicine, 2015, 372: 2018-2028.
Goodman et al., "PD-1-PD-L1 immune-checkpoint blockade in B-cell lymphomas," Nature reviews clinical oncology, 2017 14(4): 203-220.
Gray et al., "An accurate, precise method for general labeling of extracellular vesicles," MethodsX, 2015, 2: 360-367.
Greening et al., "A protocol for exosome isolation and characterization: evaluation of ultracentrifugation, density-gradient separation, and immunoaffinity capture methods," Methods Mol Biol, 2015, 1295:179-209.
Grigor'Eva et al., "Contamination of exosome preparations, isolated from biological fluids," Biomed Khim, 2017, 63(1): 91-96.
Gu et al., "Clinical significance of urine prostatic exosomal protein in the diagnosis of prostate cancer," Am J Cancer Res, 2019, 9(5): 1074-1078.
Gulley et al., "Immunotherapy biomarkers 2016: overcoming the barriers," Journal of Immunotherapy Cancer, 2017, 5: Article No. 29.
Guo et al., "Exosomes: Potent regulators of tumor malignancy and potential bio-tools in clinical application," Crit Rev Oncol Hematol, 2015, 95(3): 346-358.
Gurunathan et al., "Review of the Isolation, Characterization, Biological Function, and Multifarious Therapeutic Approaches of Exosomes," Cells, 2019, 8(4): 307.
Haes et al., "A unified view of propagating and localized surface plasmon resonance biosensors," Anal Bioanal Chem, 2004, 379: 920-930.
Halvaei et al., Exosomes in Cancer Liquid Biopsy: A Focus on Breast Cancer, Mol Ther Nucleic Acids, 2018, 10: 131-141.
Han et al., "Single-vesicle imaging and co-localization analysis for tetraspanin profiling of individual extracellular vesicles," Journal of Extracellular Vesicles, 2021, 10(3): e12047.
Hannafon et al., "Plasma exosome microRNAs are indicative of breast cancer," Breast Cancer Res, 2016, 19: Article No. 90.
Haun et al., "Micro-NMR for rapid molecular analysis of human tumor samples," Science Translational Medicine, 2011, 3(71): 71ra16-71ra16.
Helwa et al., "A Comparative Study of Serum Exosome Isolation Using Differential Ultracentrifugation and Three Commercial Reagents," PLoS One, 2017, 12(1): 0170628.
Herbst et al., "Predictive correlates of response to the anti-PD-LI antibody MPDL3280A in cancer patients," Nature, 2014, 515: 563-567.
Ho et al., "Circulating miR-210 as a novel hypoxia marker in pancreatic cancer," 2010, 3: 109-113.
Hong et al., "Molecular signatures of circulating melanoma cells for monitoring early response to immune checkpoint therapy," Proceedings of the National Academy of Sciences of the United States of America, 2018, 115: 2467-2472.
Hu et al., "A signal-amplifiable biochip quantifies extracellular vesicle-associated RNAs for early cancer detection," Nat Commun, 2017, 8: 1683.
Huang et al., "Homogeneous, Low-volume Efficient and Sensitive Quantitation of Circulating Exosomal PD-LI for Cancer Diagnosis and Immunotherapy Response Prediction," Angewandte Chemie, 2020, pp. 4800-4805.
Huang et al., "Prostate-specific antigen immunosensing based on mixed self-assembled monolayers, camel antibodies and colloidal gold enhanced sandwich assays," Biosensors and bioelectronics, 2005, 21: 483-490.
Im et al., "Label-free detection and molecular profiling of exosomes with a nano-plasmonic sensor," Nat Biotechnol, 2014, 32: 490-495.
International Search Report and Written Opinion for Application No. PCT/US2020/063695 dated Mar. 4, 2021 (7 pages).
International Search Report and Written Opinion for Application No. PCT/US2021/046561 dated Dec. 17, 2021 (11 pages).
International Search Report and Written Opinion for Application No. PCT/US2022/081751 dated Jul. 3, 3023 (28 pages).
Izon, "Measure Nanoparticles with Unparalleled Precision," <https://izon.com/nanoparticlemeasurement/> webpage available as early as Apr. 15, 2021.
Jeong et al., "Integrated Magneto-Electrochemical Sensor for Exosome Analysis," ACS Nano, 2016, 10(2): 1802-1809.
Jiang et al., "EpCAM-dependent extracellular vesicles from intestinal epithelial cells maintain intestinal tract immune balance," Nat. Commun., 2016, 7: 13045.
Jotatsu et al., "PD-LI immunohistochemistry in patients with non-small cell lung cancer," J Thorac Dis, 2018, 10: 52127-52129.
Kahlert et al., "Exosomes in tumor microenvironment influence cancer progression and metastasis," J Mol Med (Berl), 2013, 91: 431-437.
Kalluri et al., "The biology, function, and biomedical applications of exosomes," Science, 2020, 367(6478): eaau6977.
Kalluri, "The biology and function of exosomes in cancer," Journal of Clinical Investigation, 2016, 126(4): 1208.
Kang et al., High-purity capture and release of circulating exosomes using an exosome-specific dual-patterned immunofiltration (ExoDIF) device, Nanoscale, 2017, 9: 13495-13505.
Kawamoto et al., "Integrin and PD-1 Ligand Expression on Circulating Extracellular Vesicles in Systemic Inflammatory Response Syndrome and Sepsis," Shock, 2019, 52: 13-22.
Keir et al., "PD-1 and its ligands in tolerance and immunity," Annu Rev Immunol, 2008, 26: 677-704.
Khazamipour et al., "Oncofetal Chondroitin Sulfate: A Putative Therapeutic Target in Adult and Pediatric Solid Tumors," Cells, 2020, 9: 818.
Kil et al., "PD-L1 Is Regulated By Interferon Gamma and Interleukin 6 through STAT1 and STAT3 Signaling in Cutaneous T-Cell Lymphoma," Blood, 2017, 130: 1458.
Kim et al., "None of us is the same as all of us: resolving the heterogeneity of extracellular vesicles using single-vesicle, nanoscale

(56) References Cited

OTHER PUBLICATIONS characterization with resonance enhanced atomic force microscope infrared spectroscopy (AFM-IR)," Nanoscale Horizons, 2018, 3: 430-438.
Ko et al., "Single EV Protein Analysis Using Immuno ddPCR (iddPCR) Amplification," Advanced Biosystems, 2020, 4: a1900307.
Koga et al., "Purification, characterization and biological significance of tumor-derived exosomes," Anticancer Res. 2005, 25(6A): 3703-3707.
Koh et al., "Exosome enrichment by ultracentrifugation and size exclusion chromatography," Front Biosci (Landmark Ed), 2018, 23(5): 865-874.
Krishnamurti et al., "HER2 in breast cancer: A review and update," Advances in Anatomic Pathology, 2014, 21(2): 100-7.
Kudalkar et al., "Coverslip Cleaning and Functionalization for Total Internal Reflection Fluorescence Microscopy," Cold Spring Harb Protoc 2016, 2016(5): pdb.prot085548.
Lässer, "Exosomes in diagnostic and therapeutic applications: Biomarker, vaccine and RNA interference delivery vehicle," Expert Opinion on Biological Therapy, 2015, 15(1): 103-17.
Laufer et al., "Rescuing the Clinical Breast Examination: Advances in Classifying Technique and Assessing Physician Competency," Annals of Surgery, 2017, 266(6): 1069-1074.
Lee et al., "Influence of Storage Condition on Exosome Recovery," Biotechnology and Bioprocess Engineering, 2016, 21: 299-304.
Lee et al., "Multiplexed Profiling of Single Extracellular Vesicles," ACS Nano, 2018, 12: 494-503.
Lennon et al., "Single molecule characterization of individual extracellular vesicles from pancreatic cancer," Journal of Extracellular Vesicles, 2019, 8: 1685634.
Li et al., "Exosomal proteins as potential markers of tumor diagnosis," Journal of Hematology and Oncology, 2017, 10: Article No. 175.
Li et al., "Exosomes play roles in sequential processes of tumor metastasis," International Journal of Cancer, 2019, 144(7): 1486-1495.
Li et al., "Progress in exosome isolation techniques," Theranostics, 2017, 7(3): 789-804.
Li et al., "Serum microRNA-21 as a potential diagnostic biomarker for breast cancer: a systematic review and meta-analysis," Clin. Exp. Med., 2016, 16(1): 29-35.
Liga et al., "Exosome isolation: a microfluidic road-map," Lab Chip, 2015, 15: 2388-94.
Lin et al., "Exosomes : Novel Biomarkers for Clinical Diagnosis," Scientific World Journal, 2015, 2015: 657086.
Liu et al., "Single-Exosome-Counting Immunoassays for Cancer Diagnostics," Nano Lett, 2018, 18: 4226-4232.
Liu et al., "λ-DNA- and Aptamer-Mediated Sorting and Analysis of Extracellular Vesicles," J Am Chem Soc, 2019, 141: 3817-3821.
Lobb et al., "Optimized exosome isolation protocol for cell culture supernatant and human plasma," J. Extracell. Vesicles, 2015, 4: 27031.
Lou et al., "Construction of Potential Glioblastoma Multiforme-Related miRNA-mRNA Regulatory Network," Frontiers in Molecular Neuroscience, 2019, 12: 66.
Lyon et al., "Surface Plasmon Resonance of Au Colloid-Modified Au Films: Particle Size Dependence," The Journal of Physical Chemistry B, 1999, 103: 5826-5831.
Macías et al., "Comparison of six commercial serum exosome isolation methods suitable for clinical laboratories . Effect in cytokine analysis," Clinical Chemistry and Laboratory Medicine, 2019, 57: 1539-1545.
Mandrekar, "Receiver operating characteristic curve in diagnostic test assessment," Journal of Thoracic Oncology, 2010, 5: 1315-1316.
Marzolf et al., "SLIMarray: Lightweight software for microarray facility management," Source Code for Biology and Medicine, 2006, 1:5.
Melero et al., "Light-Induced Molecular Adsorption of Proteins Using the PRIMO System for Micro-Patterning to Study Cell Responses to Extracellular Matrix Proteins," JoVE, 2019, e60092.
Meng et al., "FBXO38 mediates PD-1 ubiquitination and regulates anti-tumour immunity of T cells," Nature, 2018, 564: 130-135.
Min et al., "Plasmon-Enhanced Biosensing for Multiplexed Profiling of Extracellular Vesicles," Advanced Biosystems, 2020, 4: 2000003.
Minciacchi et al., "Extracellular Vesicles in Cancer: Exosomes, Microvesicles and the Emerging Role of Large Oncosomes," Seminars in Cell & Developmental Biology, 2015, 40: 41-51.
Mitchell et al., "Sensitivity enhancement of surface plasmon resonance biosensing of small molecules," Anal Biochem, 2005, 343: 125-135.
Mol et al., "Higher functionality of extracellular vesicles isolated using size-exclusion chromatography compared to ultracentrifugation," Nanomedicine 2017, 13: 2061-2065.
Momen-Heravi et al., "Current methods for the isolation of extracellular vesicles," Biological Chemistry, 2013, 394: 1253-1262.
Momen-Heravi, "Isolation of Extracellular Vesicles by Ultracentrifugation," Methods Mol. Biol., 2017, 1660: 25-32.
Motzer et al., "Nivolumab versus everolimus in advanced renal-cell carcinoma," New England Journal of Medicine, 2015, 373: 1803-1813.
Musante et al., "Proteases and protease inhibitors of urinary extracellular vesicles in diabetic nephropathy," J. Diabetes Res, 2015, 2015: 289734.
O'Brien et al., "RNA delivery by extracellular vesicles in mammalian cells and its applications," Nat Rev Mol Cell Biol, 2020, 21: 585-606.
Onitilo et al., "Breast Cancer Subtypes Based on ER/PR and Her2 Expression: Comparison of Clinicopathologic Features and Survival," Clin. Med. Res., 2009, 7: 4-13.
Pan et al., "A simple procedure to improve the surface passivation for single molecule fluorescence studies," Phys Biol, 2015, 12: 045006.
Pang et al., "Personalized detection of circling exosomal PD-L1 based on Fe3O4@TiO2 isolation and SERS immunoassay," Biosens Bioelectron, 2020, 148: 111800.
Pereira de Oliveira Jr. et al., "Detection of Extracellular Vesicle RNA Using Molecular Beacons," iScience, 2020, 23(1): 100782.
Pisitkun et al., "Identification and Proteomic Profiling of Exosomes in Human Urine," Proc. Natl. Acad. Sci. U. S. A., 2004, 101: 13368.
Poggio et al., "Suppression of Exosomal PD-LI Induces Systemic Anti-tumor Immunity and Memory," Cell, 2019, 177: 414-427 e413.
Qin et al., "New advances in immunotherapy for non-small cell lung cancer," American Journal of Translational Research, 2018, 10: 2234-2245.
Ramirez et al., "Technical challenges of working with extracellular vesicles," Nanoscale, 2018, 10: 881-906.
Raposo et al., "Extracellular Vesicles: Exosomes, Microvesicles, and Friends," J. Cell Biol, 2013, 200: 373.
Reátegui et al., "Engineered nanointerfaces for microfluidic isolation and molecular profiling of tumor-specific extracellular vesicles," Nature Communications, 2018, 9: 175.
Reategui et al., "Tunable nanostructured coating for the capture and selective release of viable circulating tumor cells," Adv Mater, 2015, 27: 1593-1599.
Rekker et al., "Comparison of Serum Exosome Isolation Methods for MicroRNA Profiling," Clin. Biochem., 2014, 47: 135.
Ribas, "Adaptive immune resistance: how cancer protects from immune attack," Cancer Discovery, 2015, 5(9): 915-919.
Ricardo et al., "Breast cancer stem cell markers CD44, CD24 and ALDH1: Expression distribution within intrinsic molecular subtype," J. Clin. Pathol., 2011, 64(11): 937-946.
Ricklefs et al., "Immune evasion mediated by PD-L1 on glioblastoma-derived extracellular vesicles," Science Advances, 2018, 4: eaar2766.
Rima et al., "Surface engineering within a microchannel for hydrodynamic and self-assembled cell patterning," Biomicrofluidics, 2020, 14: 014104.

(56) References Cited

OTHER PUBLICATIONS

Rogers et al., "Annexin A1-dependent tethering promotes extracellular vesicle aggregation revealed with single-extracellular vesicle analysis," Science Advances, 2020, 6: eabb1244.
Roy et al., "A practical guide to single-molecule FRET," Nat Methods, 2008, 5: 507-516.
Rupp et al., "Loss of EpCAM expression in breast cancer derived serum exosomes: Role of proteolytic cleavage," Gynecol. Oncol., 2011, 122(2): 437-446.
Sadahiro et al., "Activation of the Receptor Tyrosine Kinase AXL Regulates the Immune Microenvironment in Glioblastoma," Cancer Research, 2018, 78: 3002.
Saliminejad et al., "Why have microRNA biomarkers not been translated from bench to clinic?" Future Oncology, 2020, 15: 1773-1781.
Schultz et al., "TKTL1 is overexpressed in a large portion of non-small cell lung cancer specimens," Diagnostic Pathology, 2008 3: 35.
Schwartz et al., "Introduction to Tangential Flow Filtration for Laboratory and Process Development Applications," PALL Corp., 2014, 13 pages.
Schwarzenbach, "Clinical relevance of circulating, cell-free and Exosomal microRNAs in plasma and serum of breast cancer patients," Oncology Research and Treatment, 2017, 40: 423-429.
Seymour et al., "iRECIST: guidelines for response criteria for use in trials testing immunotherapeutics," The Lancet Oncology, 2017, 18: e143-e152.
Shao et al., "Chip-based analysis of exosomal mRNA mediating drug resistance in glioblastoma," Nat Commun, 2015, 6: 6999.
Shao et al., "Protein typing of circulating microvesicles allows real-time monitoring of glioblastoma therapy," Nature Medicine, 2012, 18: 1835-1840.
Sharma et al., "Immunoaffinity-based isolation of melanoma cell-derived exosomes from plasma of patients with melanoma," J. Extracell. Vesicles, 2018, 7: 1435138.
Shen et al., "A Single Extracellular Vesicle (EV) Flow Cytometry Approach to Reveal EV Heterogeneity," Angewandte Chemie, 2018, 57: 15675-15680.
Sheridan, "Exosome cancer diagnostic reaches market," Nature Biotechnology, 2016, 34(4): 359-60.
Shimomura et al., "Novel combination of serum microRNA for detecting breast cancer in the early stage," Cancer Sci., 2016, 107: 326-334.
Shrivastava et al., "Methods for the determination of limit of detection and limit of quantitation of the analytical methods," Chronicles of Young Scientists, 2011 2: 21.
Shukuya et al., "Circulating MicroRNAs and Extracellular Vesicle-Containing MicroRNAs as Response Biomarkers of Anti-programmed Cell Death Protein 1 or Programmed Death-Ligand 1 Therapy in NSCLC," J Thorac Oncol, 2020, 15: 1773-1781.
Simpson, R. J., Lim, J. W. E. & Moritz, R. L. Exosomes : proteomic insights and diagnostic potential. 6, 267-283 (2009).
Sims et al., "Origins of breast cancer subtypes and therapeutic implications," Nature Clinical Practice Oncology, 2007, 4(9): 516-525.
Skliar et al., "Imaging of Extracellular Vesicles by Atomic Force Microscopy," J. Vis. Exp., 2019, 151: e59254.
Smith et al., "Urinary biomarkers predict brain tumor presence and response to therapy," Clin. Cancer Res., 2008, 14: 2378-2386.
Sorensen et al., "Increase in soluble PD-1 is associated with prolonged survival in patients with advanced EGFR-mutated non-small cell lung cancer treated with erlotinib," Lung cancer, 2016, 100: 77-84.
Soung et al., "Exosomes in cancer diagnostics," Cancers, 2017, 9(1): 8.
Spectrum Laboratories, "MicroKros and MidiKros Hollow Fiber membranes for Tangential Laboratory Separations," Product Information & Operating Instructions, 2013, 19 pages.
Springer et al., "Enhancing sensitivity of surface plasmon resonance biosensors by functionalized gold nanoparticles: size matters," Anal Chem, 2014, 86: 10350-10356.
Stauffer et al., "EzColocalization: An ImageJ plugin for visualizing and measuring colocalization in cells and organisms," 2018, 8: 1-13.
Strale et al., "Multiprotein printing by light-induced molecular adsorption," Adv Mater, 2016, 28: 2024-2029.
Stranska et al., "Comparison of membrane affinity—based method with size—exclusion chromatography for isolation of exosome—like vesicles from human plasma," J. Transl. Med., 2018, 16(1): 1.
Su et al., "Upregulated expression of serum exosomal miR-375 and miR-1307 enhance the diagnostic power of CA125 for ovarian cancer," Journal of Ovarian Research, 2019, 12: 6.
Sun et al., "Autocalibrated scanning-angle prism-type total internal reflection fluorescence microscopy for nanometer-precision axial position determination," Anal Chem, 2010, 82: 2441-2447.
Syn et al., "Exosomes in Cancer Nanomedicine and Immunotherapy: Prospects and Challenges," Trends in Biotechnology, 2017, 35(7): 665-676.
Ter-Ovanesyan et al., "Imaging of Isolated Extracellular Vesicles Using Fluorescence Microscopy," Extracellular Vesicles: Methods and Protocols, 2017, pp. 233-241.
Theodoraki et al., "Clinical Significance of PD-L1(+) Exosomes in Plasma of Head and Neck Cancer Patients," Clin Cancer Res, 2018, 24: 896-905.
Théry et al., "Exosomes: Composition, Biogenesis and Function," Nat. Rev. Immunol., 2002, 2: 569.
Théry et al., "Isolation and Characterization of Exosomes from Cell Culture Supernatants," Curr. Protoc. Cell Biol., 2006, Chapter 3, Unit 3.22.
Théry et al., "Minimal information for studies of extracellular vesicles 2018 (MISEV2018): a position statement of the International Society for Extracellular Vesicles and update of the MISEV2014 guidelines," J Extracellular Vesicles, 2018, 7: 1535750.
Tian et al., "Nanoparticle Counting by Microscopic Digital Detection: Selective Quantitative Analysis of Exosomes via Surface-Anchored Nucleic Acid Amplification," Anal Chem, 2018, 90: 6556-6562.
Tian et al., "Quality and efficiency assessment of six extracellular vesicle isolation methods by nano-flow cytometry," Journal of Extracellular Vesicles, 2019, 9: 1697028.
Uludag et al., "Cancer biomarker detection in serum samples using surface plasmon resonance and quartz crystal microbalance sensors with nanoparticle signal amplification," Anal Chem, 2012, 84: 5898-5904.
Van der Pol et al., "Particle size distribution of exosomes and microvesicles determined by transmission electron microscopy, flow cytometry, nanoparticle tracking analysis, and resistive pulse sensing," Journal of Thrombosis and Haemostasis, 2014, 12: 1182-1192.
Verdegaal et al., "Neoantigen landscape dynamics during human melanoma-T cell interactions," Nature, 2016, 536: 91.
Wang et al., "Extracellular mRNA detected by molecular beacons in tethered lipoplex nanoparticles for diagnosis of human hepatocellular carcinoma," PLoS One, 2018, 13: e0198552.
Wang et al., "Multiple myeloma exosomes establish a favourable bone marrow microenvironment with enhanced angiogenesis and immunosuppression," J. Pathol., 2016, 239(2): 162-173.
Wang et al., "Recent advances in single extracellular vesicle detection methods," Biosens Bioelectron, 2020, 154: 112056.
Weisman et al., "Nanostructure of cationic lipidoligonucleotide complexes," Biophysical Journal, 2004, 87: 609-614.
Westphal et al., "Circulating biomarkers for gliomas," Nature Reviews Neurology, 2015, 11: 556-566.
Wolchok et al., "Nivolumab plus ipilimumab in advanced melanoma," New England Journal of Medicine, 2013, 369: 122-133.
Wu et al., "Detection of extracellular RNAs in cancer and viral infection via tethered cationic lipoplex nanoparticles containing molecular beacons," Anal Chem, 2013, 85: 11265-11274.
Wu et al., Exosomes: improved methods to characterize their morphology, RNA content, and surface protein biomarkers, Analyst, 2015, 140: 6631-6642.

(56) References Cited

OTHER PUBLICATIONS

Wu et al., "Profiling surface proteins on individual exosomes using a proximity barcoding assay," Nature Communications, 2019, 10: 3854.
Wu et al., "Smoking Induced Extracellular Vesicles Release and Their Distinct Properties in Non-Small Cell Lung Cancer," J Cancer, 2019, 10: 3435-3443.
Wu et al., "sRNAnalyzer—a flexible and customizable small RNA sequencing data analysis pipeline," Nucleic Acids Research, 2017, 45: 12140-12151.
Xie et al., "Altered miRNA expression in sputum for diagnosis of non-small cell lung cancer," Lung Cancer, 2010, 67: 170-176.
Xu et al., "Extracellular vesicle isolation and characterization: Toward clinical application," Journal of Clinical Investigation, 2016, 26(4): 1152-1162.
Xu et al., "Extracellular vesicles in cancer implications for future improvements in cancer care," Nat Rev Clin Oneal, 2018, 15(10): 617-638.
Yáñez-Mó et al., "Biological Properties of Extracellular Vesicles and Their Physiological Functions," J. Extracell. Vesicles, 2015, 4: 27066.
Yang et al., "Diagnostic accuracy of urine protein/creatinine ratio is influenced by urine concentration," PLoS One, 2015, 10(9): e0137460.
Yang et al., "Exosome separation using microfluidic systems: size-based, immunoaffinity-based and dynamic methodologies," Biotechnol. J., 2017, 12: 1600699.
Yang et al., "Interferometric plasmonic imaging and detection of single exosomes," Proceedings of the National Academy of Sciences, 2018, 115: 10275-10280.
Yang et al., "Large-scale generation of functional mRNA-encapsulating exosomes via cellular nanoporation," Nature Biomedical Engineering, 2020, 4: 69-83.
Yekula et al., "From laboratory to clinic: Translation of extracellular vesicle based cancer biomarkers," Methods, 2020, 177: 58-66.
Yoo et al., "A direct extraction method for microRNAs from exosomes captured by immunoaffinity beads," Anal. Biochem., 2012, 431(2): 96-98.
Yu et al., "Detection of Exosomal PD-L1 Rna in Saliva of Patients With Periodontitis," Front Genet, 2019, 10: 202.
Yuana et al., "Co-isolation of extracellular vesicles and high-density lipoproteins using density gradient ultracentrifugation," J Extracell Vesicles, 2014, 3(1): 23262.
Yuana et al., "Cryo-electron microscopy of extracellular vesicles in fresh plasma," J Extracell Vesicles, 2013, 2: 21494.
Zeng et al., "Tumour exosomes from cells harbouring PTPRZ1-MET fusion contribute to a malignant temozolomide chemoresistance in glioblastoma," Oncogene, 2017, 36: 5369-5381.
Zhang et al., "Exosomes in cancer: small particle, big player," Journal of Hematology & Oncology, 2015, 8: 83.
Zhang et al., "Immunomagnetic sequential ultrafiltration (iSUF) platform for enrichment and purification of extracellular vesicles from biofluids," Scientific Reports, 2021, 11: 8034.
Zhang et al., "Liquid Biopsy for Cancer: Circulating Tumor Cells, Circulating Free DNA or Exosomes?," Cell. Physiol. Biochem., 2017, 41(2): 755-768.
Zhou et al., "Collection, storage, preservation, and normalization of human urinary exosomes for biomarker discovery," Kidney Int., 2006, 69: 1471-1476.
Zhou et al., "High-throughput single-EV liquid biopsy: Rapid, simultaneous, and multiplexed detection of nucleic acids, proteins, and their combinations," Science Advances, 2020, 6: eabc1204.
Zhu et al., "Circulating microRNAs in breast cancer and healthy subjects," BMC Res Notes, 2009, 2: 89.
Zhu et al., "Soluble PD-1 and PD-L1: predictive and prognostic significance in cancer," Oncotarget, 2017, 8: 97671.
Ziaei et al., "Review: Isolation and Detection of Tumor-Derived Extracellular Vesicles," ACS Appl. Nano Mater., 2018, 1: 2004-2020.
Zieren et al., "Extracellular vesicle isolation from human renal cancer tissue," Medical Oncology, 2020, 37: 28.
Zottel et al., "Analysis of miR-9-5p, miR-124-3p, miR-21-5p, miR-138-5p, and miR-1-3p in Glioblastoma Cell Lines and Extracellular Vesicles," International Journal of Molecular Sciences, 2020, 21: 8491.
Benedikter et al., Ultrafiltration Combined with Size Exclusion Chromatography Efficiently Isolates Extracellular Vesicles from Cell Culture Media for Compositional and Functional Studies, Scientific Reports, 2017, 7: 15297.
Strale et al., "Light-Induced quantitative microprinting of biomolecules," Proc. of SPIE, 2017, 10117: 8 pages.
Zhang et al., "Engineering a Single Extracellular Visicle Protein and RNA Assay (siEV PRA) via In Situ Fluorescence Microscopy in a UV Micropattered Array," bioRxiv, 2022, Retrieved from <https://www.biorxiv.org/content/10.1101/2022.08.05.502995v1.full>.
United States Patent Office Action for U.S. Appl. No. 17/778,765 dated Oct. 17, 2025 (16 pages).
European Patent Office Action for Application No. 21859087.5 dated Jul. 14, 2025 (4 pages).

* cited by examiner

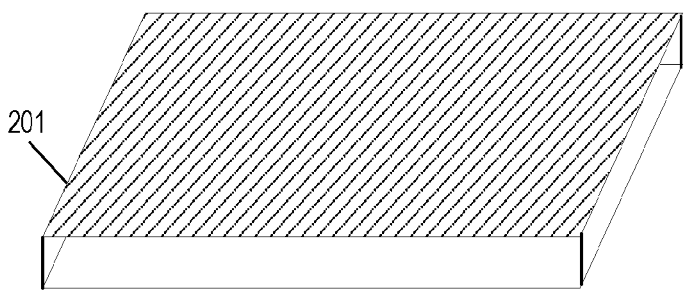
FIG. 2A
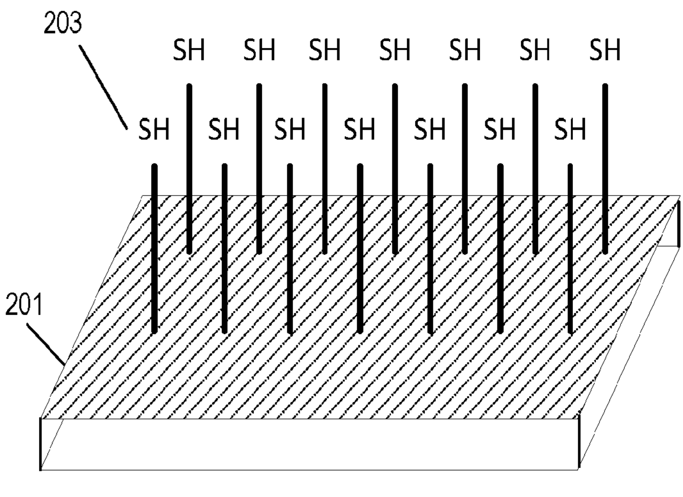
FIG. 2B
205
201
FIG. 2C

Scale bars = 50 μm

Responder
Non-responder
Healthy donor
Protein
mRNA
10 µm

FIG. 8A

Responder

Non-responder

Healthy donor

Protein mRNA

HIGHLY SENSITIVE PLATFORM TO CHARACTERIZE EXTRACELLULAR VESICULAR BIOMARKERS FOR CANCER IMMUNOTHERAPY

CROSS-REFERENCE TO RELATED APPLICATION(S)

This application is a U.S. national stage entry of International Patent Application No. PCT/US2021/046561, filed on Aug. 18, 2021, which claims priority to U.S. Provisional Patent Application No. 63/067,531, filed on Aug. 19, 2020, the entire contents of each of which are fully incorporated herein by reference.

BACKGROUND

The present invention relates to systems and methods for characterizing extracellular vesicular biomarkers.

SUMMARY

In one embodiment, the invention provides a biochip to characterize extracellular vesicular biomarkers for cancer immunotherapy. The biochip includes a glass surface, a gold film layer on the glass surface, a plurality of gold nanoparticles coupled to the gold film layer, and a plurality of biotinylated antibodies coupled to the gold nanoparticles. The biotinylated antibodies are selected to capture specific types of extracellular vesicles. In some implementations, the gold film layer of the biochip is coated with polyethylene glycol (PEG).

Other aspects of the invention will become apparent by consideration of the detailed description and accompanying drawings.

BRIEF DESCRIPTION OF THE DRAWINGS

FIG. 2A is a schematic diagram of a cleaned glass slide used to produce the nanogold biochip of FIG. 1.

FIG. 2B is a schematic diagram of the cleaned glass slide of FIG. 2A after treatment with a binding material that acts as glue between the glass slide and a gold layer.

FIG. 2C is a schematic diagram of the treated glass slide of FIG. 2B after a gold layer is deposited.

FIG. 8A is a sequence of TIRF images of EVs captured by the nanogold biochip as shown in FIG. 3B for PD-L1 protein and mRNA for cancer patients that respond to immunotherapy, cancer patients that do not respond to immunotherapy, and a healthy donor.

FIG. 12A is a sequence of TIRF images for PD-L1 protein and PD-L1 mRNA captured by the nanogold biochip using CD63/CD9 as the capture antibodies for healthy donors, non-responders, and responders.

DETAILED DESCRIPTION

Figure 1:
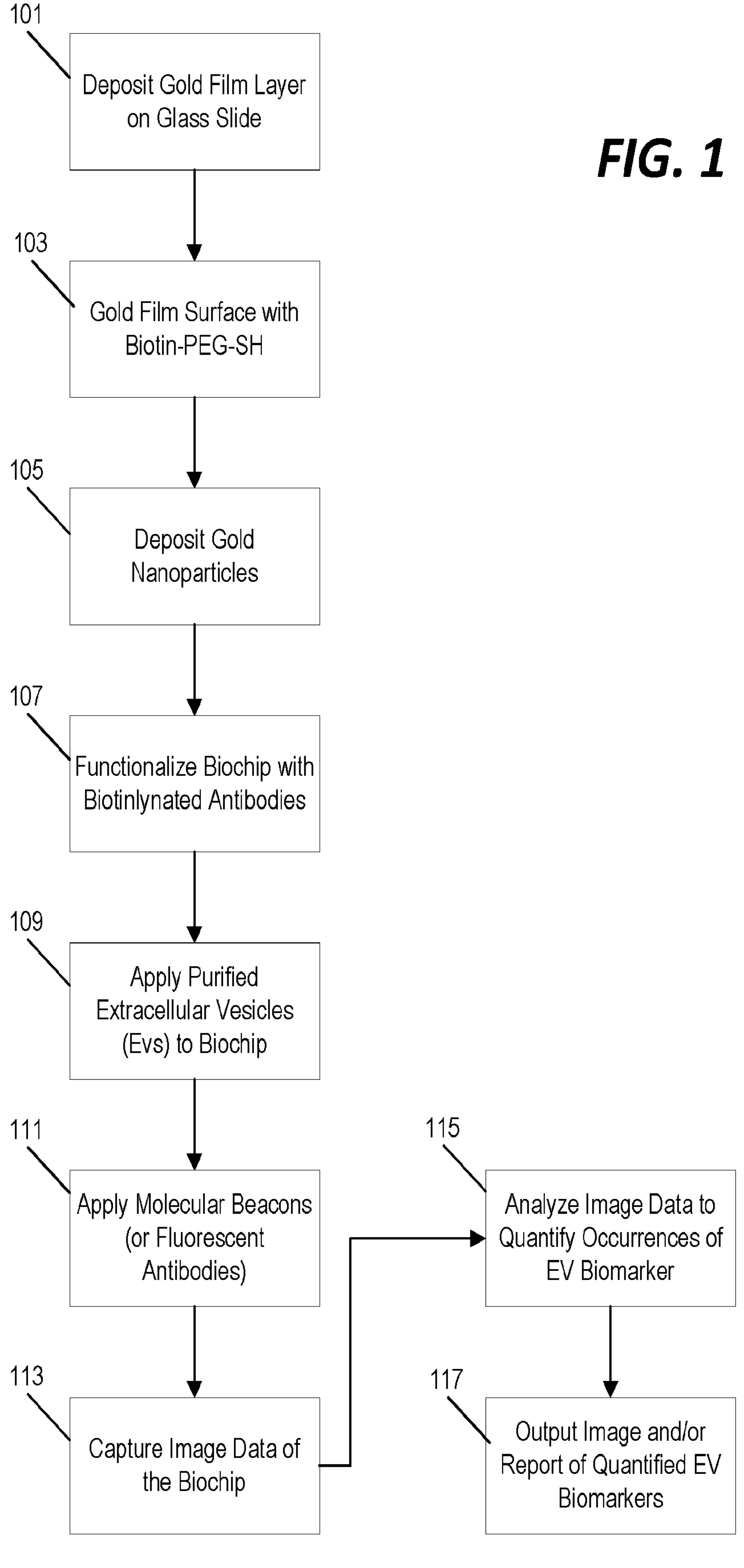
FIG. 1 is a flowchart of a method for producing a biochip with gold nanoparticles and for quantifying extracellular vesicular biomarkers using the nanogold biochip.

Before any embodiments of the invention are explained in detail, it is to be understood that the invention is not limited in its application to the details of construction and the arrangement of components outlined in the following description or illustrated in the following drawings. The invention is capable of other embodiments and of being practiced or of being carried out in various ways.

The immune system responds to cancer via a complex network of cellular interactions in which cytotoxic T-cells, helper T-cells, and natural killer cells are activated and work in concert against tumor cells. However, many metastatic tumors have adopted methods to hijack immune checkpoints to evade immune recognition. One of the recently discovered pathways is the overexpression of programmed cell death ligand 1 (PD-L1) on the surface of tumor cells which binds to programmed cell death protein 1 (PD-1) on T-cells leading to blockade of T-cell activation and protecting tumor cells from T cell-mediated killing. The manipulation of immune checkpoints or pathways by using immune checkpoint inhibitors (ICIs) has emerged as an essential and effective form of immunotherapy and demonstrated successes due to positive and durable clinical trial outcomes. For instance, patients with metastatic melanoma treated with concurrent ipilimumab (anti-cytotoxic T lymphocyte-associated molecule-4 (CTLA-4)) and nivolumab (anti-PD-1) achieved an overall survival rate of 79% at two years. However, the majority of unselected patients do not respond to immunotherapy, for example, the response rate to single-agent PD-1/PD-L1 inhibition in patients with renal cell carcinoma is only 19%. Hence, there is a major challenge and unmet need to determine which individual patients may benefit from PD-1/PD-L1 blockade as well as other immunotherapeutics.

Tumor PD-L1 expression has been approved by FDA as a predictive biomarker for immunotherapy and detected using immunohistochemistry (IHC). Four PD-L1 IHC assays using four different PD-L1 antibodies (22C3, 28-8, SP263, SP142) on two different automated staining platforms (Dako and Ventana) have been registered with FDA. Patients with higher expression of PD-L1 on their biopsies are associated with improved response rates to PD-1/PD-L1 blockade. Following initiation of checkpoint inhibitor therapy, repeating sampling of tumor biopsies is necessary to monitor the response to immunotherapy. Serial tumor biopsies are invasive with potentially serious complications, and the sampling at a single metastatic site may not represent the entire tumor burden in a highly heterogeneous cancer. Hence, there is an unmet need to detect those predictive biomarkers in a non-invasive manner via liquid biopsies such as blood and urine. This approach will help to integrate signals from all metastatic foci and can be repeated serially throughout immunotherapy.

Extracellular vesicles (EVs) are lipid particles released from cells, varying from 50 nm to a few microns and including a) exosomes generated inside multivesicular endosomes, b) microvesicles shed from the plasma membrane, and c) oncosomes differentiated from apoptotic cellular bodies. They contain different cargos, including proteins, RNA, DNA and lipids, which can be trafficked between cells and serve as mediators of intercellular communication. The most common techniques to characterize RNAs and proteins in EVs are polymerase chain reaction (PCR), next-generation sequencing (NGS), mass spectroscopy (MS), western blot, enzyme-linked immunosorbent assay (ELISA), and flow cytometry. However, these existing methods primarily focus on bulk analysis, which requires many EVs with limited resolution and sensitivity. Compared to abundant biomarkers in EVs (like tetraspanins CD9, CD63, CD81, etc.), quantification of low-abundant biomarkers is challenging. There have been some efforts to characterize PD-1/PD-L1 proteins and PD-L1 RNA from EVs using western blot, flow cytometry and PCR; however, to the best of our knowledge, there have been no studies co-quantify these molecular contents (proteins and RNAs) from EVs up to now. The combination of these molecular contents would provide a more comprehensive profiling of EVs from cancer patients.

We have recently developed biochip platforms to isolate tumor EVs specifically and sensitively detect EV-encapsulated target RNAs using cationic lipoplex nanoparticles (CLNs) containing target-specific molecular beacons (MBs). These technologies have been shown to successfully capture and characterize bulk EVs from different cancers and non-cancerous conditions. However, to quantify low-abundant biomarkers for immunotherapy, a more sensitive platform that enables on-chip single EV characterization is needed. In this work, we aim to develop a highly sensitive immunoaffinity-based platform for co-quantification of PD-1/PD-L1 proteins and mRNAs in EVs derived from non-small cell lung cancer (NSCLC) patient blood. The high sensitivity is achieved by characterization at the single EV level due to a combination of a biochip which maximizes signal-to-noise ratio (SNR), and a high-resolution total internal reflection fluorescence (TIRF) microscopy. The biochip was made of a glass coverslip coated with polyethylene glycol (PEG) to prevent non-specific bindings and gold spherical nanoparticles (NPs) to amplify signals and improve sensitivity. Nanoparticles (e.g., cationic lipoplex nanoparticles and gold nanoparticles) are nanoscale particles of matter between 1 and 100 nanometers in diameter. Different antibodies were tethered on the chip surface to capture and sort EVs into subpopulations based on their membrane protein compositions. PD-1/PD-L1 antibodies with a tyramide signal amplification (TSA) technology were then used to quantify the corresponding membrane protein contents on the captured single EVs. CLNs with transcript-specific probes tagged with MBs were also fused with the captured individual EVs to identify and quantify PD-1/PD-L1 mRNA in the EVs. A sensitive automated TIRF microscope was used to detect and quantify specific biomolecules based on fluorescence intensity.

FIG. 1 illustrates a method of producing a biochip and using that biochip for total internal reflection fluorescence (TIRF) microscopy. As shown in various examples described herein, high-resolution TIRF microscopy can be used in cell biology for the visualization of complex processes or the composition of single objects due to its high signal-to-noise ratio (SNR) and the capability to detect single molecules. This imaging technique restricts excitation to a precise focal plane near the coverslip and eliminates out-of-focus fluorescence, thereby allowing single-molecule detection. As also demonstrated by these examples, high-resolution TIRF microscopy can be applied to visualize extracellular vesicles (EVs) pre-stained with a fluorescent membrane dye on a glass slide. However, for on-chip EV labeling, non-specific binding of labeling antibodies to the glass coverslip can make it difficult to differentiate true binding events from the background noise. To prevent non-specific binding of biomolecules to the glass surface, the example of FIG. 1 produces and utilizes a biochip coated with polyethylene glycol (PEG) and gold nanoparticles.

In the method of FIG. 1, a gold film layer is deposited on a glass slide (step 101). In some implementations, for example, the gold film layer is coupled to the glass slide by activating the cleaned cover glass using a UV-ozone cleaner (such as, for example, UVO Cleaner Model 42, Jelight, Irvine, CA) and then modifying with the vapor of (3-mercaptopropyl) trimethoxysilane (MPTMS, Sigma-Aldrich, St. Louis, MO) for 10 minutes in a low-pressure (e.g., ~0.1 Torr) vacuum chamber. The MPTMS layer then serves as a glue layer for the deposition of a 12-nm-thick gold (Au) layer using a Denton e-beam evaporator (DV-502A, Moorsetown, NJ). In another example, the thin gold layer is deposited via titanium (thickness ~2 nm), which serves as a "metal glue" on the glass coverslip.

The gold film surface is then coated with PEG (step 103) and streptavidin-conjugated gold nanoparticles (step 105). In one specific example, the freshly prepared Au-coated glass may be transferred to a linker solution containing 1-thiahexa(ethyleneoxide) lipidic anchor molecule WC14 [20-tetradecyloxy-3, 6, 7, 12, 15, 18, 22-heptaoxahexa-tricontane-1-thioil], a lateral spacer β-mercaptoethanol (βME, Sigma-Aldrich), and biotin-PEG-SH (Nanocs, New York, NY) (molar ratio=30:69:1) in 200 proof ethanol (Fisher Scientific) for 16 hours at room temperature in the dark. In some implementations, the glass coverslip is then rinsed with ethanol to remove excess mixture physically adsorbed on the surface and air-dried. The treated glass is then attached to a 64-well tray (Grace Bio-Labs ProPlate tray set, Sigma-Aldrich) and washed thoroughly with DI water. Next, 0.01% (w/v) streptavidin-conjugated gold nanoparticles (NPs, Nanocs Inc.) in PBS are applied into the wells for 2 hours at room temperature on a rocker at 24 RPM. As described in further detail below, different sizes of gold nanoparticles may be used, and, in some implementations, the size of the gold nanoparticles may be selected to achieve a target EV capture efficacy and/or non-specific binding of antibodies.

After the gold nanoparticles are deposited, the biochip is functionalized with biotinylated antibodies (i.e., antibodies that have undergone a process of biotinylation in which biotin is attached to the antibodies) to capture a specific EV subpopulation (step 107). In some implementations, the biochip is first rinsed three times with PBS before the surface is incubated with capture antibody cocktails overnight at 4° C. on the rocker. In some implementations, for PD-L1 protein detection, a cocktail with 20 μg/mL each of recombinant chimeric EGFR monoclonal antibody (Cetuximab, Erbitux, ImClone LLC, Branchburg, NJ), a goat EpCAM/TROP-1 polyclonal antibody (#AF960, R&D Systems, Minneapolis, MN), and a goat ErbB2/Her2 polyclonal antibody (#AF1129, R&D Systems) is used. In some implementations, for PD-1 protein and PD-1/PD-L1 mRNA detection, 20 μg/mL each of a mouse CD63 monoclonal antibody (#sc-5275, Santa Cruz Biotechnology, Dallas, TX) and a mouse CD9 monoclonal antibody (#MAB1880, R&D Systems) was chosen as a capture antibody cocktail. In some implementations, these antibodies are biotinylated using an EZ-Link micro Sulfo-NHS-biotinylation kit (ThermoFischer Scientific, Waltham, MA) before the incubation. In some implementations, the device is washed three times on the next day with PBS and then blocked 3% (w/v) BSA (Sigma-Aldrich) and 0.05% (v/v) Tween-20 (Sigma-Aldrich) in PBS for 1 hour at room temperature before EV capture. In other implementations, this blocking is performed before and/or after EV capture to minimize non-specific binding further.

After the biochip is produced and functionalized with biotinylated antibodies, purified extracellular vesicles (EVs) are applied to the biochip (step 109). EVs selectively bind to the antibodies at the gold nanoparticles and molecular beacons (or other fluorescent antibodies) are then applied to bind with the captured EVs (step 111). Image data of the biochip is then captured, for example, using TIRF microscopy (step 113) and the captured image data is processed/analyzed to quantify occurrences of the EV biomarker (step 115). The TIRF image and/or report data of the quantified EV biomarkers is then output on a system display and/or stored in memory for later use (step 117).

Figure 2D:
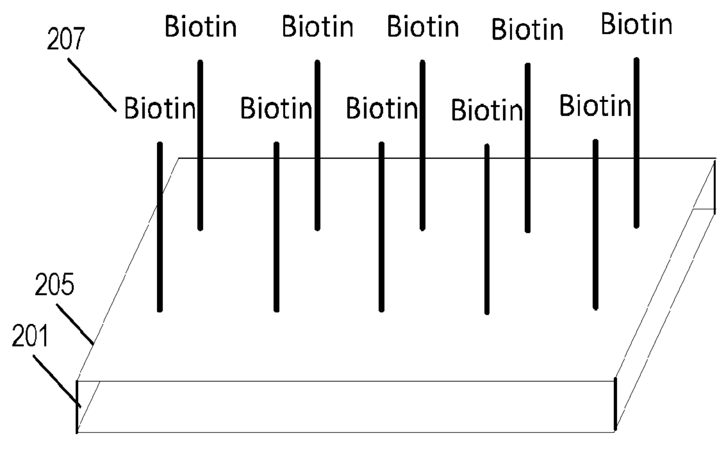
FIG. 2D is a schematic diagram of the gold-coated glass slide of FIG. 2C after treatment with a linker solution including biotin-PEG-SH.
Figure 2E:
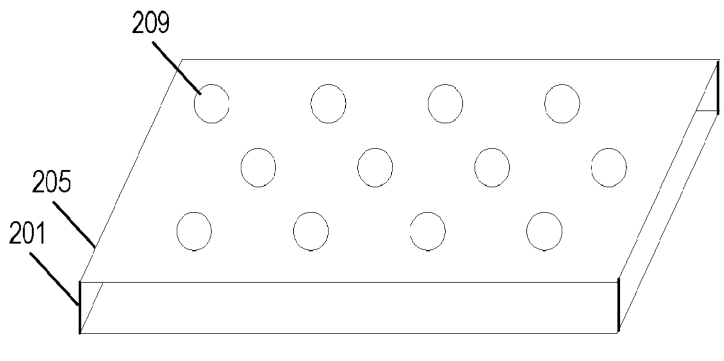
FIG. 2E is a schematic diagram of the gold-coated glass slide of FIG. 2D after gold nanoparticles are affixed thereon.
Figure 2F:
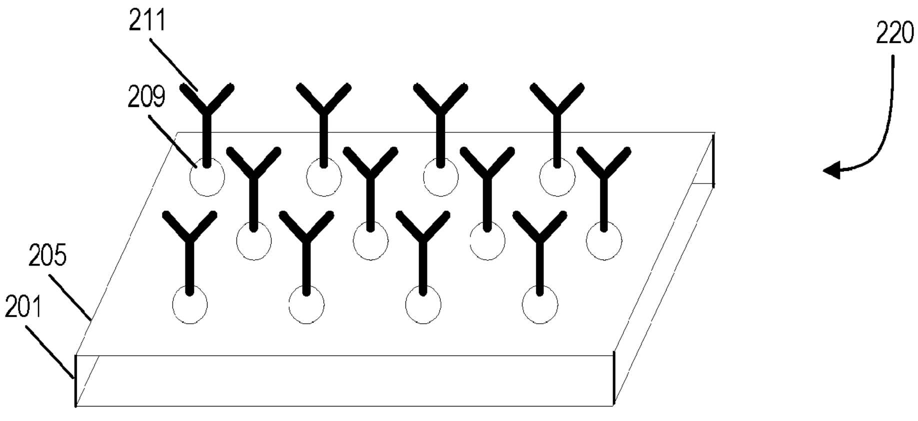
FIG. 2F is a schematic diagram of the gold-coated glass slide of FIG. 2E after incubation with biotinylated antibodies producing a nanogold biochip.

FIGS. 2A through 2F provide schematic illustrations of the biochip at various stages of the fabrication process (e.g., step 101 through step 107 in the method of FIG. 1). FIG. 2A shows the cleaned glass slide 201. After treating the slide 201 with the MPTMS, —SH mercapto groups 203 are bound to the surface of the glass slide 201 as shown in FIG. 2B, which, in turn, serves as the "glue" for coupling the thin gold layer 205 to the glass slide 201 as shown in FIG. 2C. Although MPTMS is shown in the example of FIG. 2B, in other implementations, different binding mechanisms may be used for coupling the gold layer to the glass slide. For example, as discussed above, titanium may be used instead as a "metal glue" for attaching the gold layer 205 to the glass slide 201. FIG. 2D shows the biotin layer 207 applied to the surface of the gold layer 205 on the glass slide 201 and FIG. 2E shows the gold nanoparticles 209 deposited on the surface of the gold layer 205. Finally, FIG. 2F shows the biochip 220 functionalized with the biotinylated antibodies 211 coupled to the gold nanoparticles 209. Although not illustrated in the example of FIGS. 2A through 2F, in some implementations, the functionalized biochip is attached to a structure configured to divide the surface area of the biochip into different chambers. For example, in some implementations, the biochip is attached to a silicone gasket with 64 chambers (Grace Bio-Labs, ProPlate tray set, Sigma-Aldrich).

The thin gold coating improves the SNR of TIRF microscopy through the surface plasmon resonance (SPR) effect, which takes place when total internal reflection occurs at a metal film-liquid interface. A biochip coated with a thin gold film and PEG is able to sensitively quantify target RNAs within EVs in bulk for non-invasive early cancer diagnosis. As discussed in further detail in the examples below, the inclusion of gold nanoparticles on top of the thin gold coating layer further affects the performance of the biochip in capturing EVs.

Figure 3A:
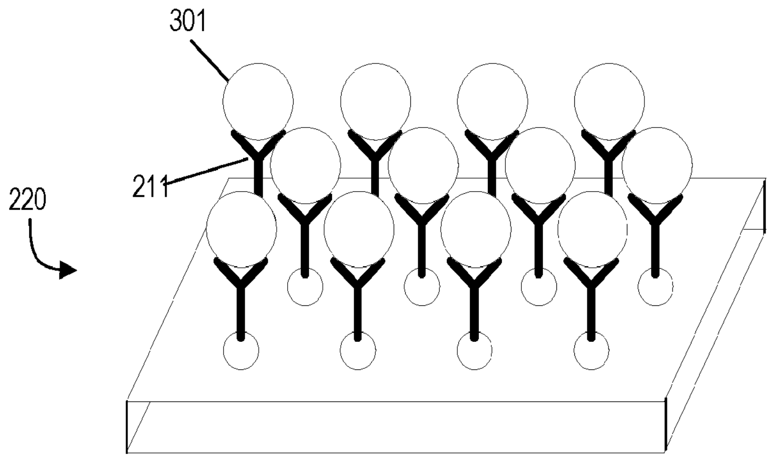
FIG. 3A is a schematic diagram of the nanogold biochip of FIG. 2F after the biotinylated antibodies capture extracellular vesicles.
Figure 3B:
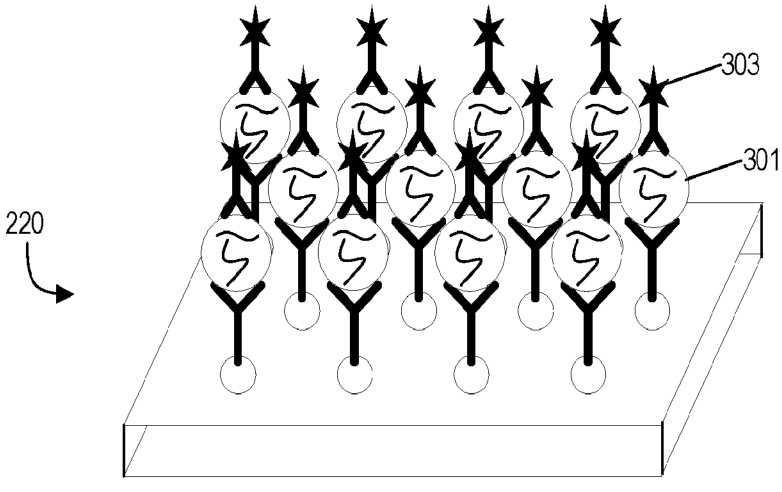
FIG. 3B is a schematic diagram of the nanogold biochip of FIG. 3A after fluorescent antibodies (or molecular beacons) bind to the captured extracellular vesicles.

FIGS. 3A and 3B schematically illustrate an example of using the biochip 220 for capture and visualization of target EVs. The functionalized biochip 220 is exposed to a sample (e.g., a biofluid) and, as shown in FIG. 3A, target EVs 301 from the sample bind to the antibodies 211 on the biochip 220. After the EVs 301 are captured by the biochip 220, fluorescent antibodies or molecular beacons 303 bind to the captured EVs 301. When TIRF images of the biochip 220 are captured, the molecular beacons 303 are visible in the captured image data. The number and/or intensity of the molecular beacons 303 visible in the captured TIRF images can then be used to characterize and quantify various aspects of the sample related to presence and/or concentrations of particular EVs.

In some of the examples described herein, the surface topography of devices coated with different sizes of streptavidin-conjugated gold NPs may be characterized using an atomic force microscope (Asylum Research MFP-3D-BIO AFM, Oxford Instruments, Abingdon, United Kingdom). Before imaging, the devices were rinsed thoroughly with deionized (DI) water to avoid salt crystals and then air-dried.

H1568 cells (NCI-H1568, ATCC® CRL-5876™, Manassas, VA) were cultured in a growth medium containing RPMI 1640 (ThermoFisher Scientific), 10% (v/v) fetal bovine serum (FBS, Sigma-Aldrich) and 1% (v/v) penicillin-streptomycin (PS, ThermoFisher Scientific). The medium was replaced every 2 to 3 days, and cultures were maintained in a humidified incubator at 37° C. with 5% CO2. When the cells reached 80%-90% confluence, they were detached using TrypLE™ express enzyme (ThermoFisher Scientific) and passaged at 1:3-1:6 ratios. H1568 cells at passages 6-10 were used in this study.

For PD-L1 staining of cells, H1568 cells were seeded at a density of 105 cells/mL in 16-well chambers (Grace Bio-Labs ProPlate® tray set) attached to a glass slide (Fisher Scientific). To stimulate PD-L1 expression, the cells were incubated with 100 ng/ml recombinant human IFN-γ (Peprotech, Rocky Hill, NJ) in the growth medium for 48 hr. The cells without IFN-γ stimulation were employed as a control. After that, they were fixed in 10% (v/v) formaldehyde (Fisher Scientific) for 15 min at RT and then permeabilized with ice-cold 100% methanol for 10 min at −20° C. A blocking buffer containing 5% (v/v) normal goat serum (ThermoFisher Scientific) and 0.3% (v/v) Triton X-100 (Sigma-Aldrich) in phosphate-buffered saline (PBS) was subsequently applied to the samples for 1 hr at RT. Rabbit PD-L1 monoclonal antibody (#86744S, Cell Signaling Technology, Danvers, MA) was diluted 200-fold in an antibody dilution buffer (1% (w/v) BSA and 0.3% (v/v) Triton X-100 in PBS) and then incubated with the cells overnight at 4° C. The next day, the cells were rinsed three times in PBS for 5 min each and subsequently incubated with a goat anti-rabbit IgG (H+L) secondary antibody—Alexa Fluor® 647 conjugate (Cell Signaling Technology) at a dilution of 1:500 in the antibody dilution buffer, for 1 hr in the dark at RT. After washing three times with PBS for 5 min each, the glass slide was detached and mounted onto a cover glass (Fisher Scientific) using ProLong™ Gold Antifade Mountant with DAPI (ThermoFisher Scientific). The images were taken using a fluorescence microscope (Nikon Eclipse Ti2, Nikon, Melville, NY).

For EVs purification from cell culture supernatants, H1568 cells were first grown to 80% confluency in the growth medium, then washed with PBS and changed to an RPMI medium supplemented with 10% (v/v) EVs-depleted FBS, 1% (v/v) PS and 100 ng/mL IFN-γ for 48 hr. EVs isolated from the medium without IFN-γ supplement were used as controls. EVs-depleted FBS was the filtrate produced from FBS through tangential flow filtration (TFF) with a 500 kDa molecular weight cut-off (MWCO) hollow fiber filter (polysulfone, Repligen, Waltham, MA). After collection, the culture supernatants were centrifuged at 1000 rpm for 2 min (Centrifuge 5810R, Eppendorf, Hauppauge, NY) to remove cell debris.

Blood samples were obtained with informed consent from healthy donors and cancer patients using an approved Institutional Review Board protocol at The Ohio State University. Blood samples from stage IV NSCLC patients were collected before they underwent immunotherapy. Serum was separated from blood using a BD Vacutainer™ SST™ Serum Separation Tube (#367985, Fisher Scientific) according to the manufacturer's protocol. 150 μL serum was diluted to 50 mL with PBS before purification.

The prepared cell supernatants and sera were firstly filtered through 1 μm filters (GE Healthcare Whatman™ Puradisc GMF, Fisher Scientific). They were subsequently concentrated and diafiltrated using TFF with the 500 kDa filter for purification. After TFF, the retentates were concentrated to 1 mL using centrifugal units (10 kDa MWCO, MilliporeSigma™ Amicon™ Ultra Centrifugal Filter Unit, Fisher Scientific) at 3000×g for 20 min. The concentration of EVs were quantified using a tunable resistive pulse sensing (TRPS) technology (qNano Gold instrument, Izon Science, Medford, MA) with NP150 (target size range 70-420 nm) and NP600 (target size range 275-1570 nm) nanopore membranes.

For CD63 detection of EVs, EVs produced from H1568 cells without IFN-γ stimulation were adjusted to a concentration of 1010 particles/mL. Thereafter, 20 μL purified EVs were applied onto devices coated with different NP sizes. PBS was used as a blank control. The following incubation and washing steps were performed at RT on the rocker. EVs were captured for 2 hr, washed three times with PBS, and then blocked with 3% (w/v) BSA and 0.05% (v/v) Tween® 20 in PBS for 1 hr. The samples were subsequently incubated with a mouse CD63 monoclonal antibody (MX-49.129.5)—Alexa Fluor® 488 conjugate (#sc-5275 AF488, Santa Cruz Biotechnology) at a dilution of 1:200 in 1% (w/v) BSA in PBS for 1 hr. Next, the devices were rinsed three times with 0.05% (v/v) Tween® 20 in PBS, and their images were taken using a TIRF microscope (Nikon Eclipse Ti Inverted Microscope System). The images were recorded by an Andor iXon EMCCD camera with a 100× oil lens at the same laser power and exposure time. For each sample, 100 (10×10 arrays) images were collected.

For PD-1/PD-L1 protein detection of EVs, 20 μL purified EVs from H1568 cells (with and without IFN-γ stimulation) and blood samples (healthy donors and cancer patients) were captured onto devices coated with 30 nm streptavidin-conjugated gold NPs for 2 hr. PBS was used as a blank control, and also a washing buffer. All incubation and washing steps were conducted at RT on the rocker. After capture, the samples were rinsed three times and stained for PD-1/PD-L1 proteins using an Alexa Fluor™ 647 Tyramide SuperBoost™ kit (#B40926, ThermoFisher Scientific). Firstly, the EVs were fixed with 10% (v/v) formaldehyde for 10 min. After washing, 3% Hydrogen Peroxide Solution was added to quench the endogenous peroxidase activity of the samples for 15 min, followed by incubation with 3% (w/v) BSA and 0.05% (v/v) Tween® 20 in PBS for 1 hr. The PD-L1 antibody (diluted 500-fold in Blocking Buffer) or rabbit PD-1 monoclonal antibody (#86163S, Cell Signaling Technology, diluted 1000-fold in Blocking Buffer) was then diluted incubated for 1 hr. Next, the samples were washed three times for 10 min each before incubation with a poly-HRP-conjugated secondary antibody for 1 hr. After washing three times for 10 min each, a Tyramide Working Solution was applied for 10 min. The reaction was stopped using a Reaction Stop Reagent. Thereafter, the samples were rinsed three times and imaged using the TIRF microscope as mentioned above.

Molecular beacons (MBs) (listed 5'-3') targeting PD-1 and PD-L1 mRNAs used in this study were +GGT+CCT/iCy3/+CCT+TCA+GGG GCT GGC GCC CCT GAA GG/BHQ_2/ and +GGT+AGC/iCy3/+CCT+CAG+CCT GAC ATG AGG CTG AGG/BHQ_2/, respectively. They were designed based on NCBI reference sequence of PD-1 (NM_005018.3) and PD-L1 (NM_014143.4) using Primer3 and BLAST (Primer-BLAST) provided by NCBI-NIH. Locked nucleic acid (LNA) nucleotides (positive sign (+) bases) were incorporated into oligonucleotide strands to improve the thermal stability and nuclease resistance of MBs for incubation at 37° C. The designed MBs were custom synthesized and purified by Sigma-Aldrich. An aqueous solution of MBs in PBS was vigorously mixed with a lipid formulation of DOTAP, Cholesterol, POPC and PEG-DSPE in 200 proof ethanol, and then sonicated for 5 min using an ultrasonic bath. The MB/lipid mixture was subsequently injected into PBS, vortexed and sonicated for 5 min. Finally, it was dialyzed with 20 kDa MWCO to remove free MBs.

For PD-1/PD-L1 mRNA detection of EVs, 20 μL purified EVs from serum samples of healthy donors and cancer patients were captured onto the 30 nm—nanogold chips for 2 hr at RT. After washing with PBS, PD-1/PD-L1 CLN MBs were applied and incubated for 2 hr at 37° C. The samples were finally rinsed with PBS and imaged using the TIRF microscope.

For analysis of the captured TIRF images, all the spots in the TIRF image were firstly located with distinguished edges, and background noise was removed by Wavelet denoising method using Matlab. Net fluorescence intensity of the spot was then calculated by subtracting the mean intensity of pixels in the spot to the mean intensity of pixels surrounding the spot. Subsequently, histograms of net fluorescence intensities of all the spots were obtained and their total fluorescence intensity was also calculated.

For ELISA testing described in the examples below, PD-L1 expression levels in H1568 cells (with and without IFN-γ stimulation) and on the surface of H1568 EVs (with IFN-γ stimulation) were quantified using a PD-L1 Human ELISA kit (#BMS2212, ThermoFisher Scientific). For the cells, they were lysed in RIPA buffer (ThermoFisher Scientific) with the addition of Thermo Scientific™ Halt™ Protease and Phosphatase Inhibitor Cocktails on ice for 5 min, and then centrifuged at 14,000×g for 15 min to remove cell debris. For the EVs, they were spiked in healthy donor serum at different concentrations ranging from 0 to 1011 particles/mL. All the samples were subsequently incubated in the ELISA plate and their PD-L1 expressions were quantitatively detected according to the manufacturer's instructions. The PD-L1 concentration in the cell lysis was normalized to its total protein concentration, which was measured using a Pierce™ Rapid Gold BCA Protein Assay kit (ThermoFisher Scientific).

All in vitro experiments and assays were repeated at least three times. All clinical samples were repeated two times. Sigma Plot 14, JMP Pro 14 and Matlab R2019a were used for data analysis. The data were expressed as mean±SD and compared by Student's t-test. A p-value below 0.05 was considered statistically significant.

Figure 4A:
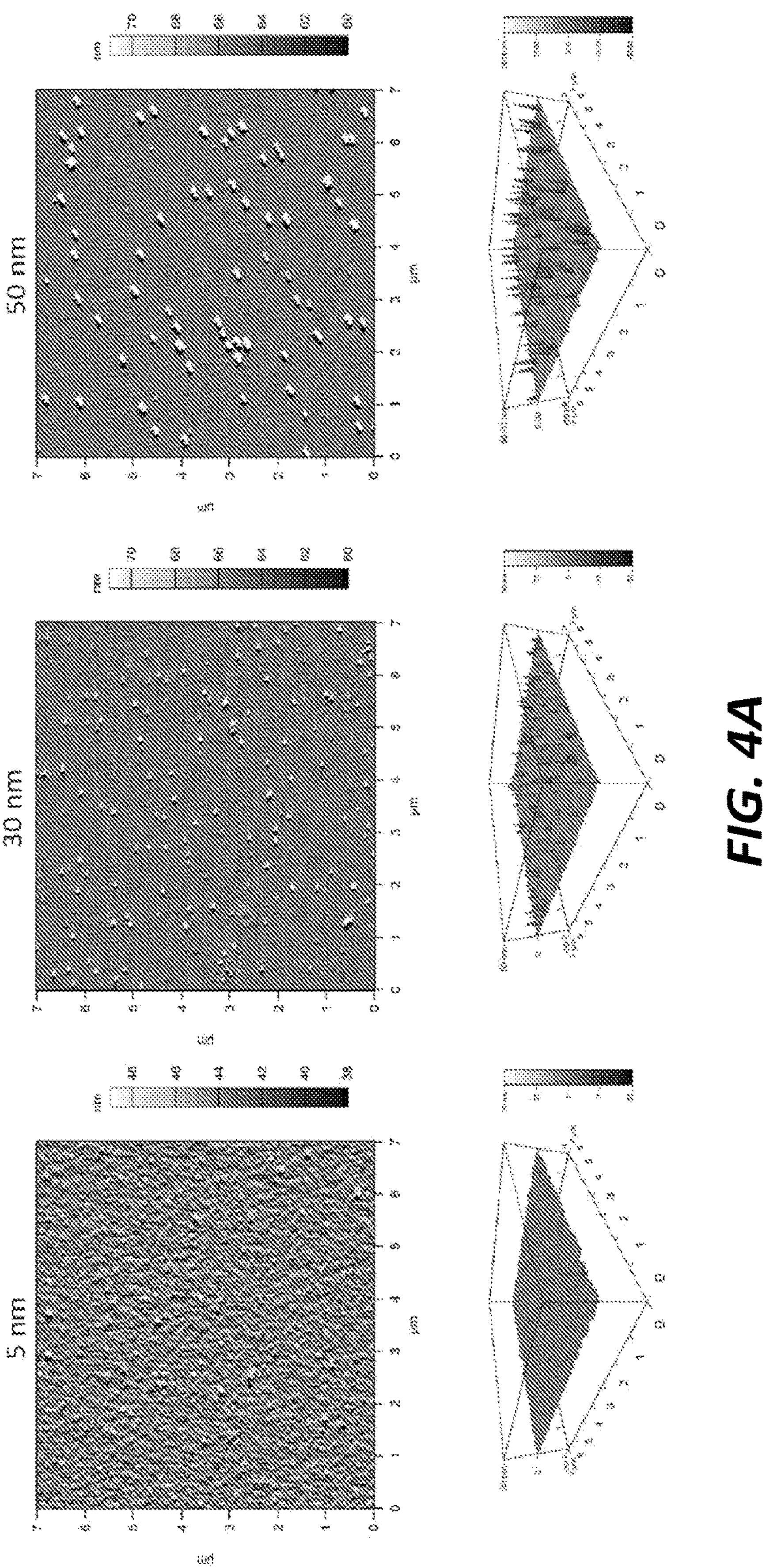
FIG. 4A is a series of atomic force microscopic (AFM) images of nanogold biochips with different-sized gold nanoparticles of 5 nm, 30 nm, and 50 nm.
Figure 4B:
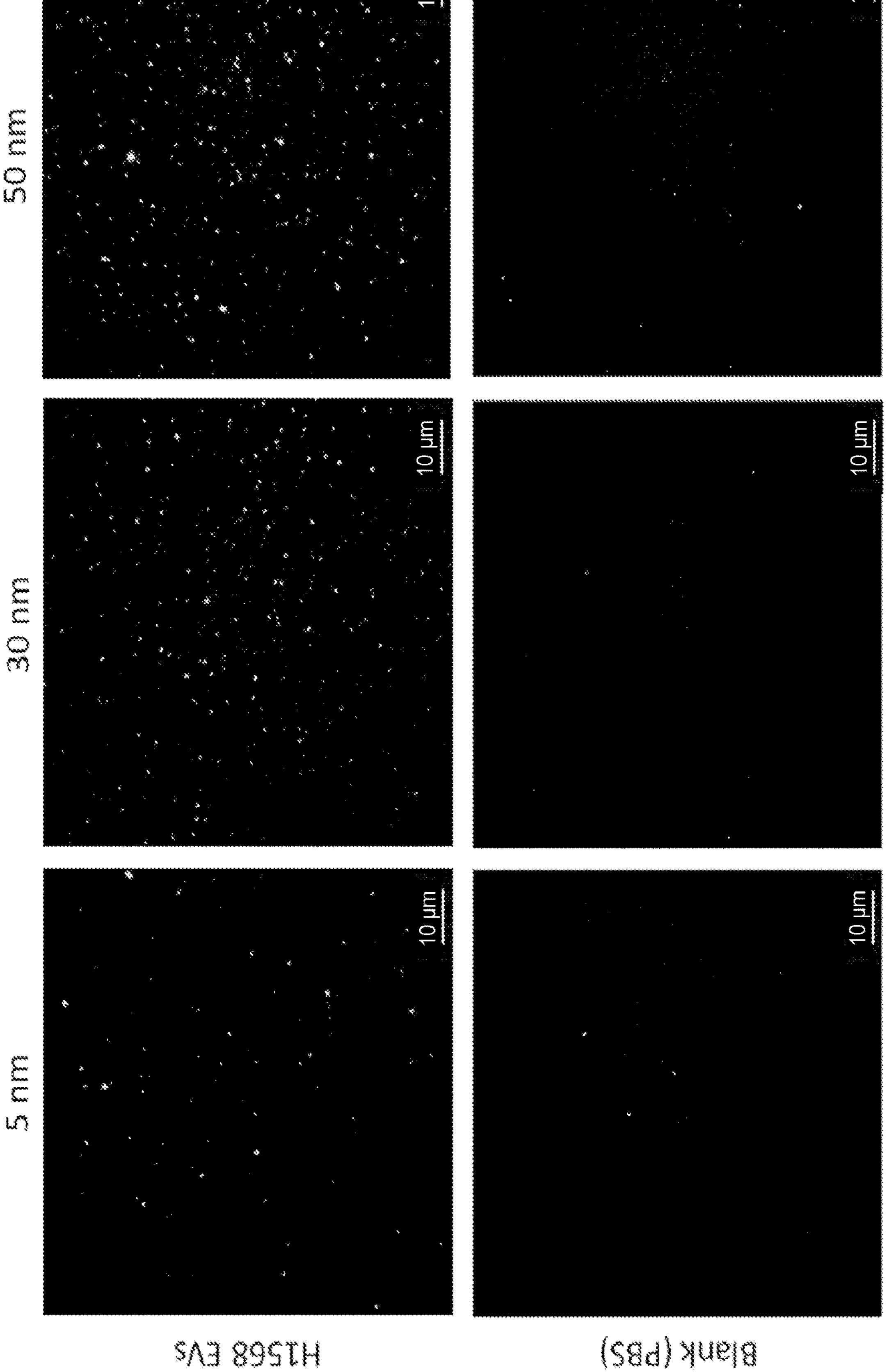
FIG. 4B is a series of total internal reflection fluorescence (TIRF) microscopy images of nanogold biochips with different-sized gold nanoparticles after capturing EVs and the blank nanogold biochips without captured EVs.
Figure 4C:
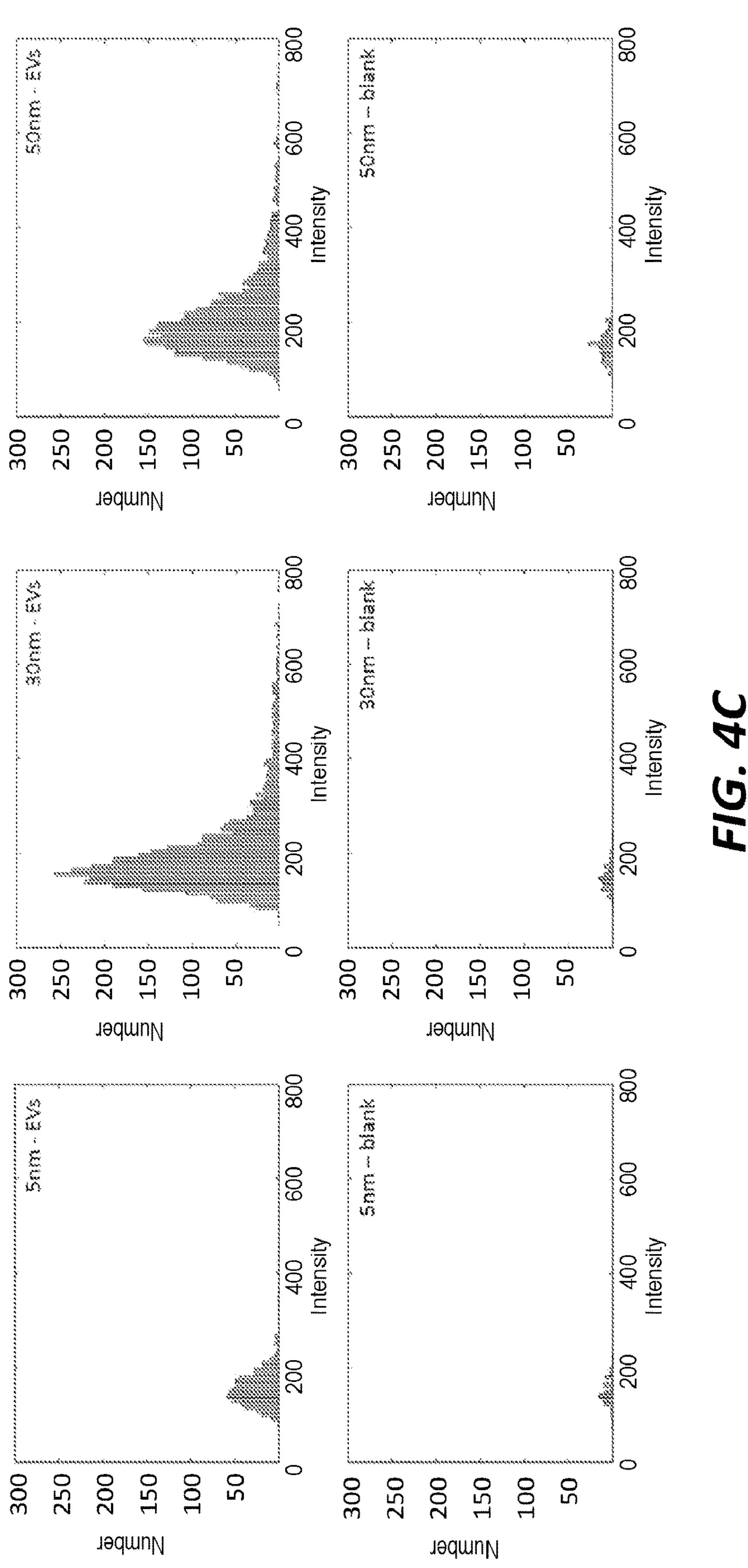
FIG. 4C is a series of intensity histograms for each of the TIRF microscopy images of FIG. 4B.
Figure 4D:
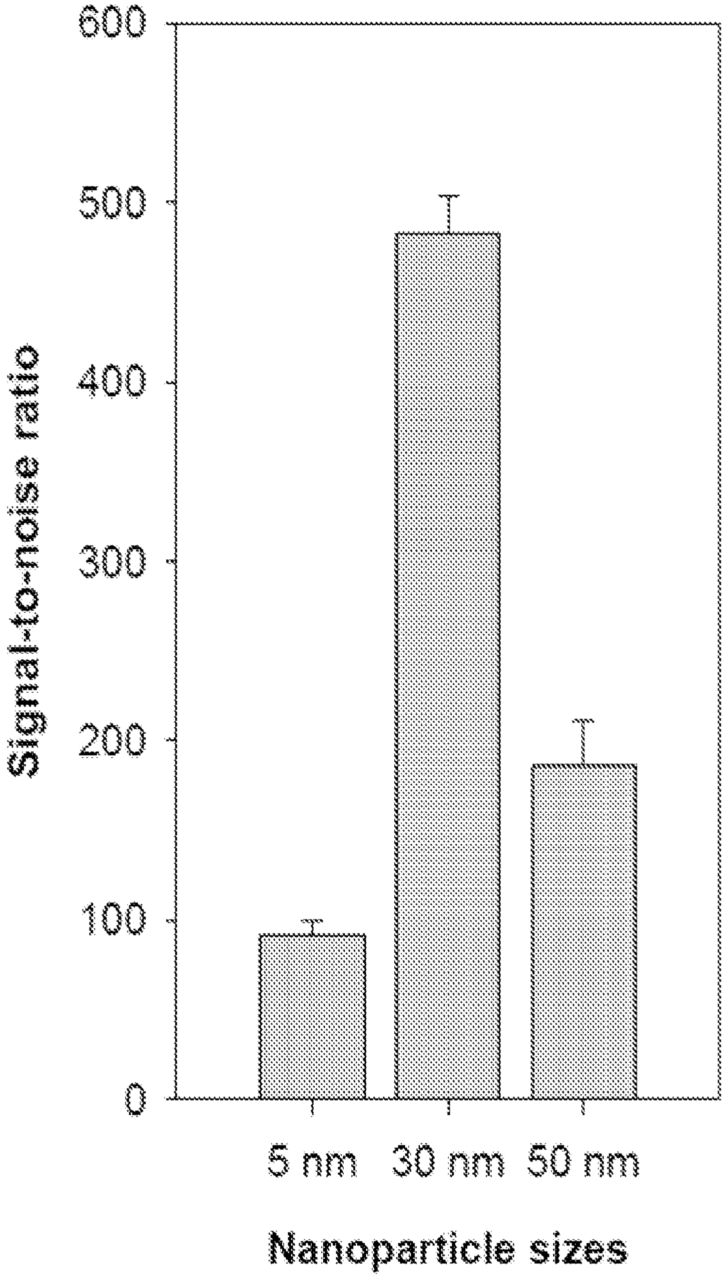
FIG. 4D is a graph of signal-to-noise ratio for different gold nanoparticles sizes based on the TIRF microscopy images of FIG. 4B.

Using the systems and methods described above, the size effect of streptavidin-conjugated gold NPs (5; 30 and 50 nm) on SNR of our platform was investigated. Atomic force microscopic (AFM) images showed that the NPs of all sizes were uniformly dispersed on the devices (FIG. 4A). With the same concentration loaded to each well (0.01% (w/v) based on gold), it is logical that the number of NPs coated on the devices decreased with the particle size. H1568, an NSCLC cell line, was used to evaluate our nanogold chip. Their purified EVs were captured on the chip using a cocktail of epidermal growth factor receptor (EGFR), epithelial cell adhesion and activating molecule (EpCAM) and human epidermal growth factor receptor 2 (Her2) biotinylated antibodies. We previously demonstrated that this cocktail facilitated the capture of a heterogeneous population of CTCs compared to single antibodies. Cluster of differentiation 63 (CD63) staining of the captured EVs were then used to evaluate the effect of NP sizes on fluorescence signal intensity and background noise. TIRF images and their histograms revealed that devices coated with 30-nm gold NPs had higher signal and lower background, while both signal and background were lower for those coated with 5-nm NPs and higher for those coated with 50-nm NPs (FIGS. 4B and 4C). Among these sizes, 30 nm was shown to produce the highest SNR ($p<0.001$, FIG. 4D). Therefore, 30-nm gold NPs were chosen for our subsequent experiments. Metal nanoparticles exhibit localized SPR, which can be seen by a strong UV-Vis absorption band that is absent from bulk metal. Gold NPs are considered to be better than other NPs for signal enhancement because they can cause higher refractive index (RI) changes and resonance angle shift. The size of gold NPs have been known to significantly affect the level of signal enhancement due to changes in surface coverage and RI. Larger NPs resulted in greater RI shift. In cancer biomarker detection using SPR biosensor, 20-nm gold NPs reduced the LOD 8 times, while 40-nm gold NPs lowered the LOD 65 times with respect to the sandwich assay. By measuring the SPR angle shift in the presence of aqueous methanol, 30 nm was found to be the optimal particle size compared to 10 and 60 nm. In another study to develop a highly sensitive nuclease-linked fluorescence oligonucleotide assay, among four different sizes tested (13; 30; 40 and 50 nm), the 40-nm gold NPs yielded the strongest signal. As such, the optimal particle size varies with devices, and in our case, it was 30 nm.

In Vitro Pd-L1 Characterization

Figure 5A:
FIG. 5A includes immunofluorescence staining images of EVs produced from H1568 cells with and without interferon-gamma (IFN-γ) stimulation.
Figure 5A:
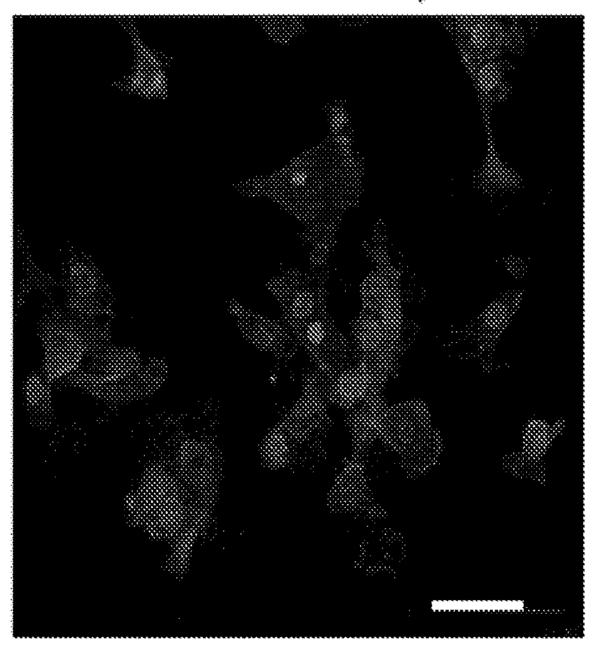
Figure 5B:
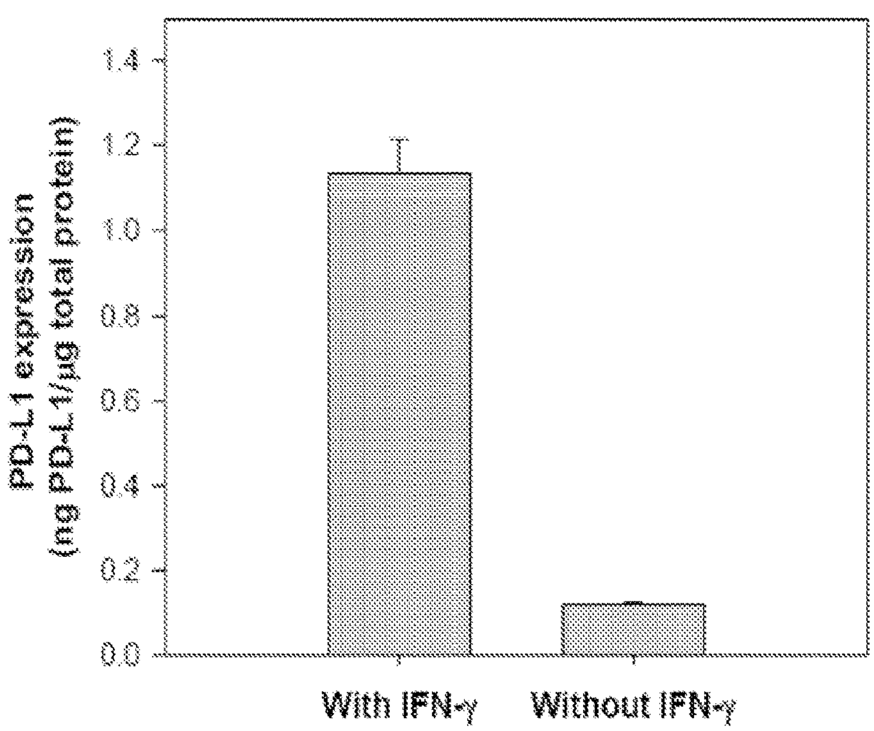
FIG. 5B is a graph of the results of an ELISA test for H1568 cells both with and without interferon-gamma (IFN-γ) stimulation.
Figure 6A:
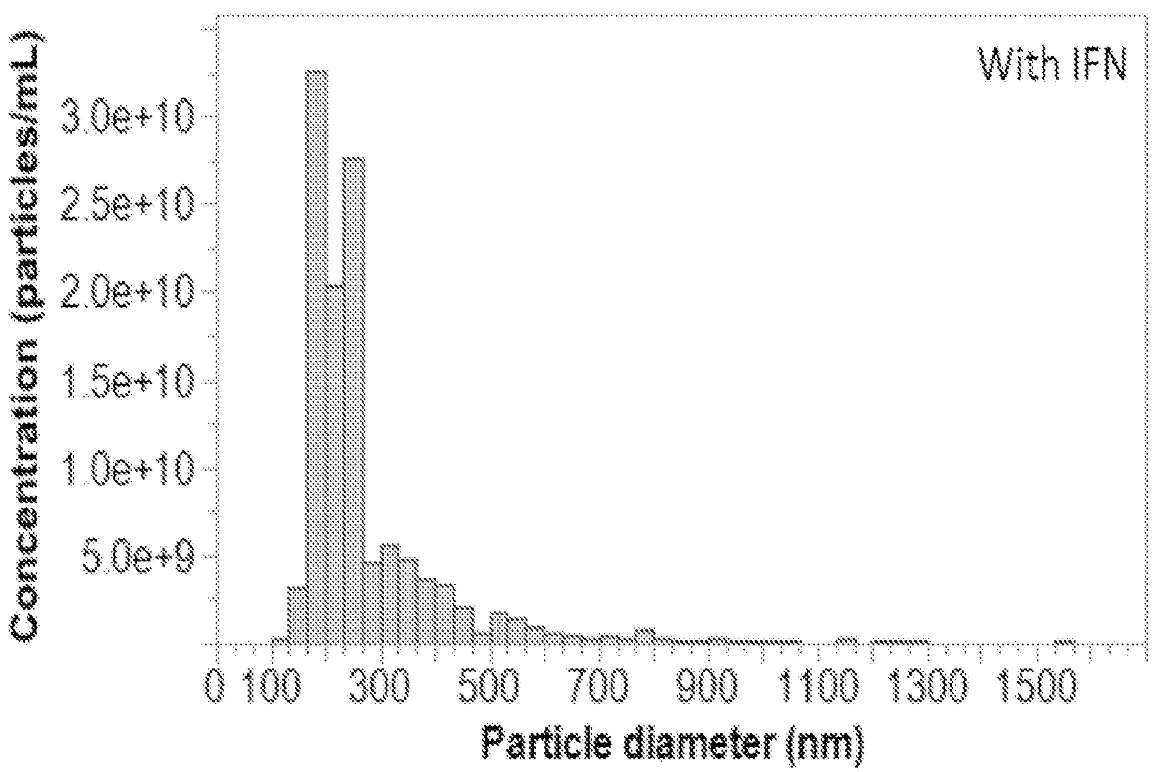
FIG. 6A is a graph of the size distribution of EVs produced by H1568 cells with interferon-gamma (IFN-γ) stimulation.
Figure 6B:
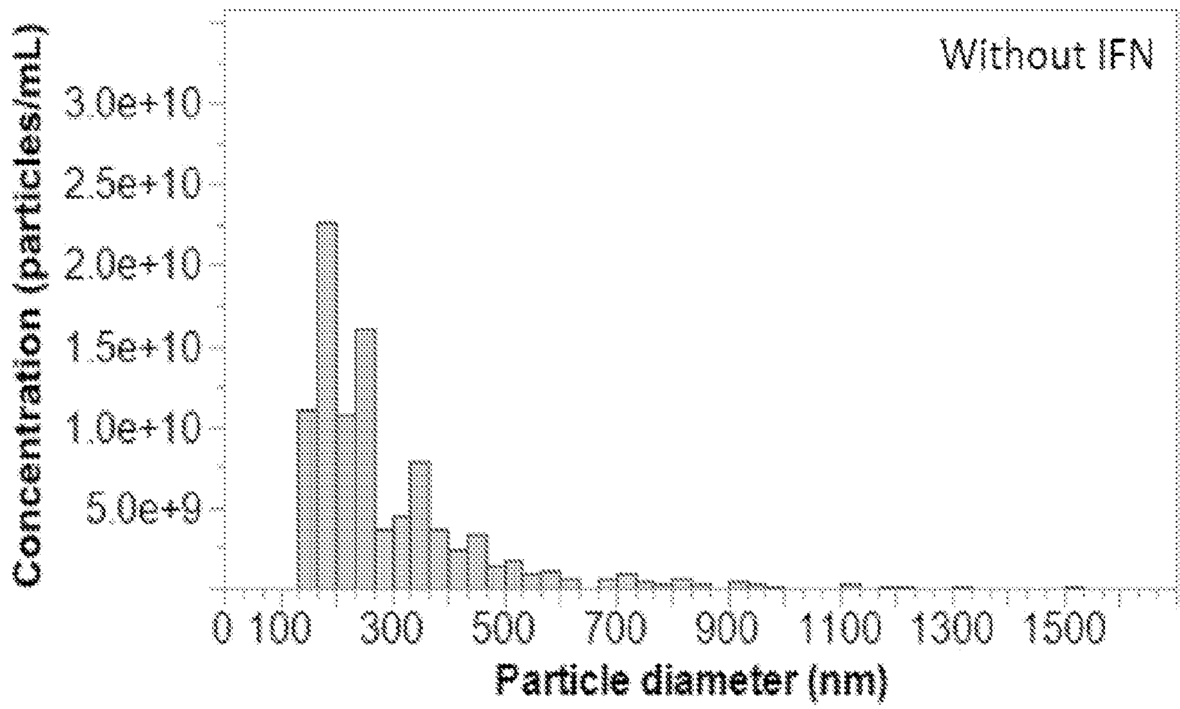
FIG. 6B is a graph of the size distribution of EVs produced by H1568 cells without interferon-gamma (IFN-γ) stimulation.
Figure 7A:
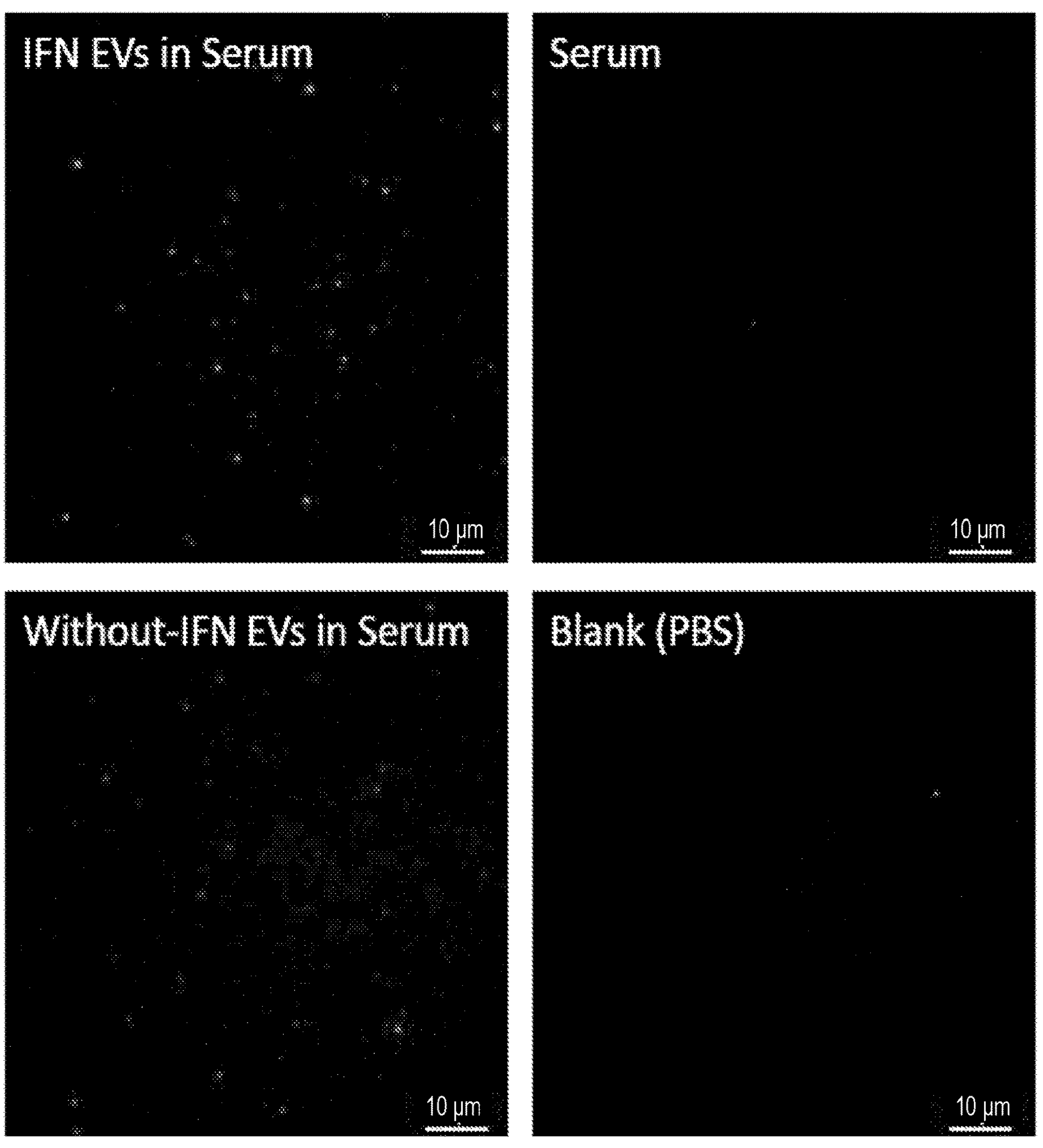
FIG. 7A is a series of TIRF microscopy images of PD-L1 expressions on H1568 EVs with and without interferon-gamma (IFN-γ) stimulation and TIRF microscopy images of the serum alone and a blank control in which PBS is used instead of EVs during the EV capture step.
Figure 7B:
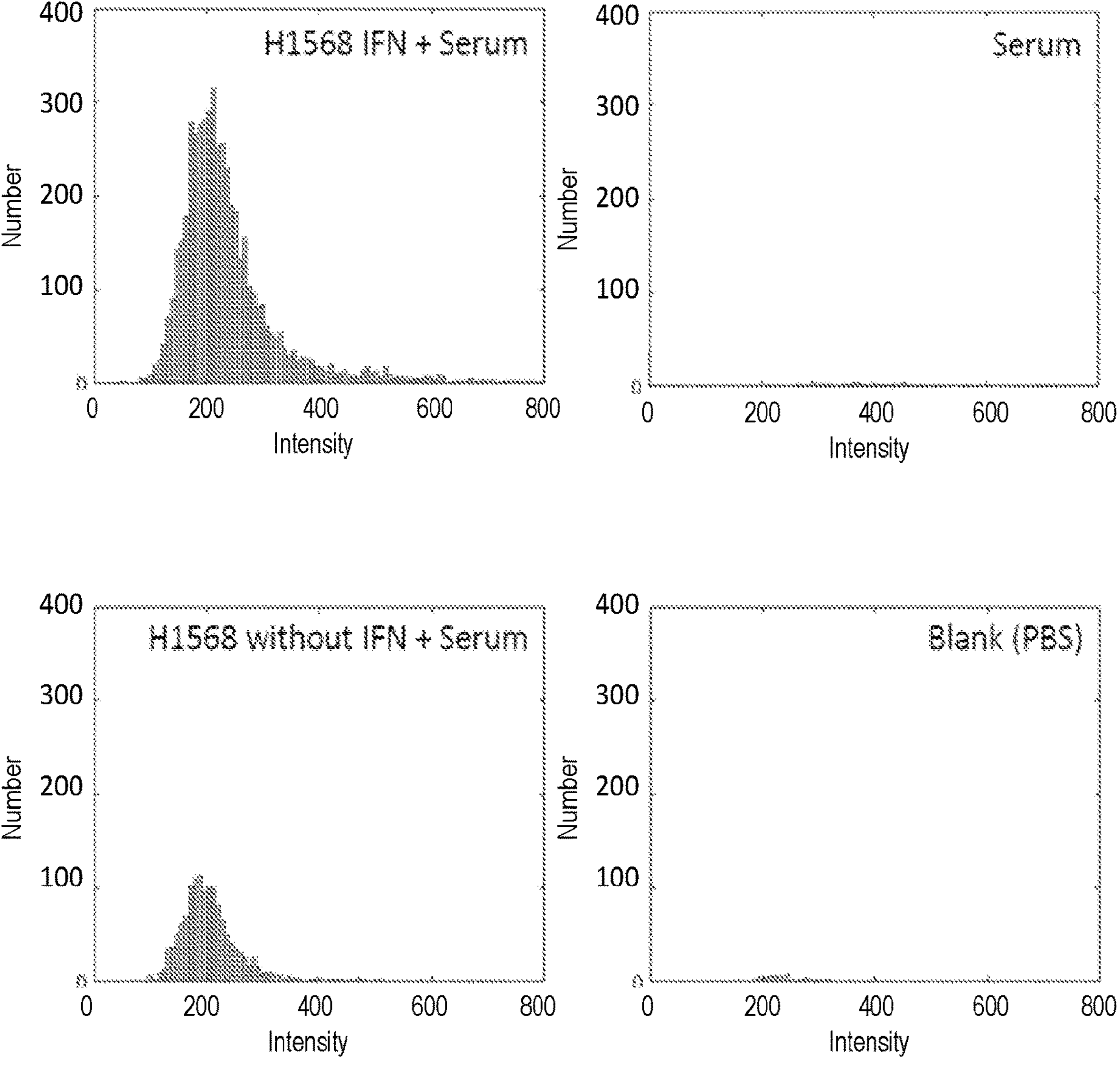
FIG. 7B is a sequence of intensity histograms for each of the TIRF images of FIG. 7A.

Interferon-gamma (IFN-γ), a cytokine secreted by activated effector T cells, is critical for innate and adaptive immunity, and known to upregulate PD-L1 expression on tumor cells. In the present study, IFN-γ also significantly increased the expression of H1568, an NSCLC cell line, as shown by immunofluorescence staining images (FIG. 5A) and ELISA test ($p<0.001$, FIG. 5B). Size distribution of EVs produced from H1568 cells with/without IFN-γ stimulation is shown in FIGS. 6A and 6B. In both cases, the majority of EVs are exosomes, which are smaller than 200 nm. These EVs were spiked in healthy donor serum at 11 ratio (tumor EVs: normal EVs) with 5×1010 particles/mL each to characterize their PD-L1 expression using our platform. Serum EVs at 5×1010 particles/mL and sample blank were also examined as negative controls. In order to quantify PD-L1 density on the EV membrane surface, there was no permeabilization buffer used in our EV staining procedures. TIRF images and their histograms showed that PD-L1 expressions on H1568 EVs with/without IFN-γ stimulation were successfully detected by our devices (FIGS. 7A and 7B). There were some signals in the blank control—in which PBS was used instead of EVs during the EV capture step, but all other staining steps were included. These signals might be derived from the device background and non-specific bindings of detection antibodies, which were optimized to be minimum. PD-L1 signals from tumor EV samples were remarkably higher than healthy donor serum. Additionally, PD-L1 expression on EVs of IFN-γ stimulated H1568 cells was considerably higher than EVs without stimulation (FIG. 7B). Previous studies revealed that, similar to cells, the levels of PD-L1 on tumor EVs were also upregulated by IFN-γ. As such, our platform was sensitive enough to differentiate PD-L1 levels on EVs of different samples.

Figure 7C:
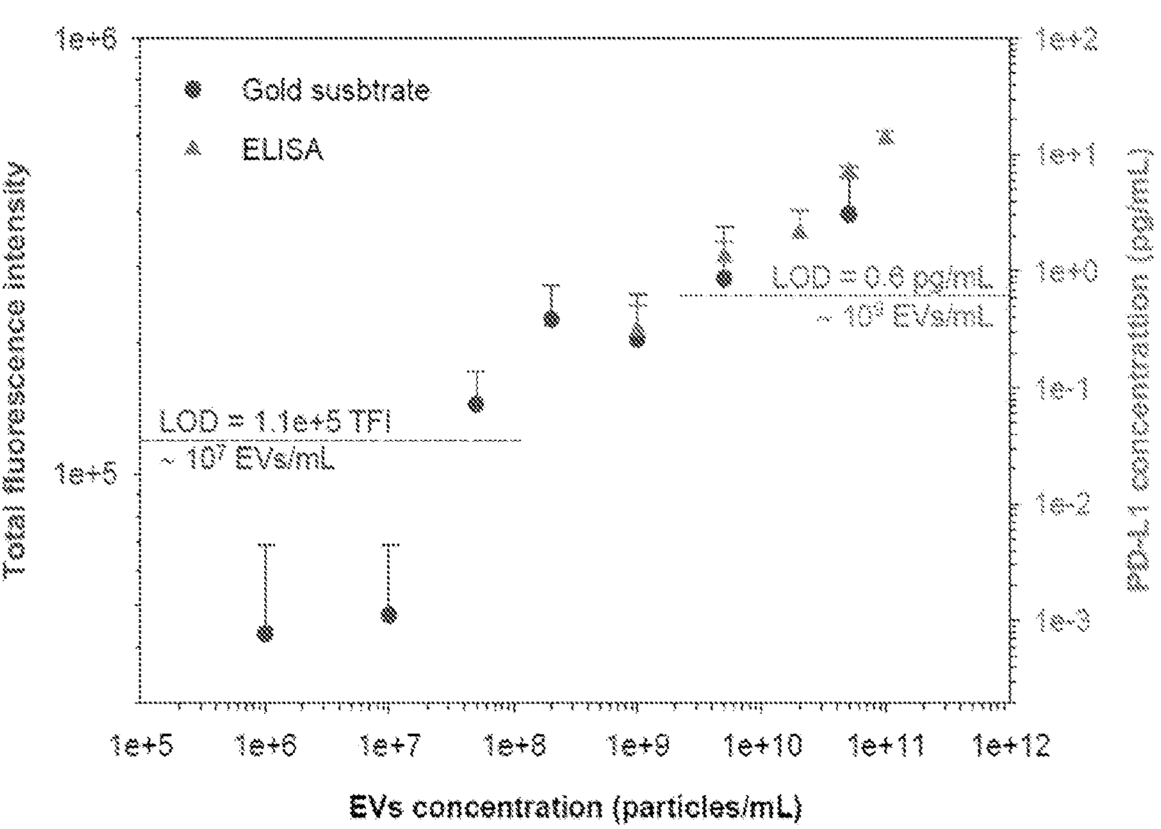
FIG. 7C is a graph of total fluorescence intensity and PD-L1 concentration as a function of EV concentration.
Figure 7D:
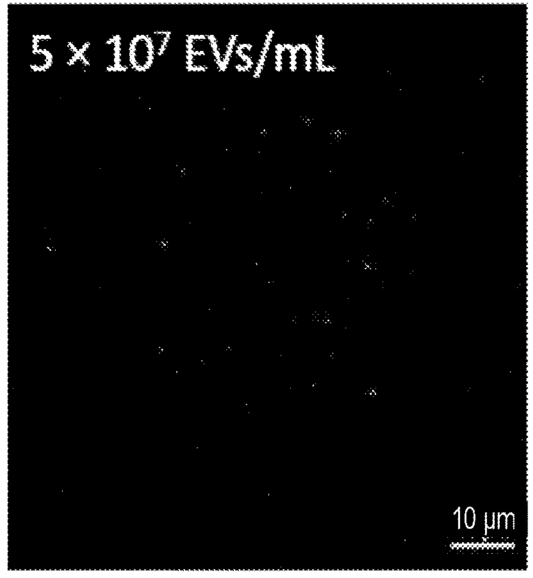
FIG. 7D is a TIRF image of PD-L1$^+$ EVs at capturing concentrations of $5\times10^7$ EVs/mL.
Figure 7E:
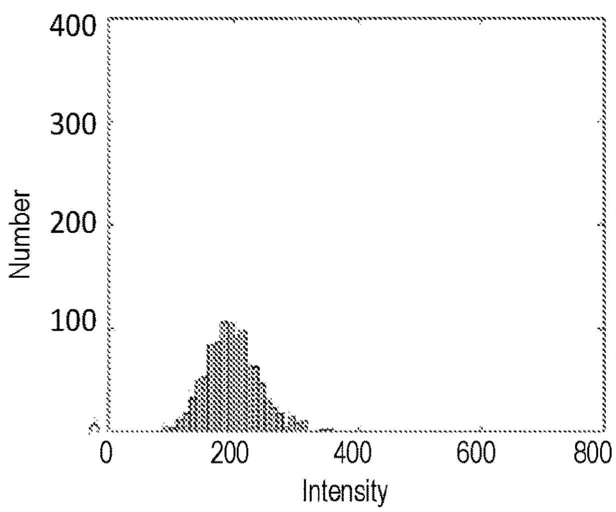
FIG. 7E is an intensity histogram of the TIRF image of FIG. 7D.

We then compared the LOD of our platform with a commercialized ELISA kit. The kit that we chose was the most sensitive kit available on the market, which has a LOD of 0.6 pg/mL. EVs produced from IFN-γ stimulated H1568 cells were spiked into healthy donor serum at different concentrations from 0 to 1011 particles/mL and quantified for PD-L1 expression using our platform and ELISA. Normal EV concentration in serum was kept constant at 1011 EVs/mL for all samples. Our results showed that while ELISA could not detect PD-L1 signal in samples with tumor EV concentrations lower than 5×109 particles/mL, our platform could detect tumor EV concentrations as low as 5×107 particles/mL (FIG. 7C). At this concentration, PD-L1 signal was greater than LOD of our platform. This value was determined using SNR method, in which a SNR of three is generally accepted for estimating LOD. The noise was defined as the standard deviation of signals obtained from blanks (by three independent experiments). As such, our platform outperformed ELISA in analytical sensitivity by 102 times. Representative TIRF images of PD-L1+EVs at capturing concentrations of 5×107 and 2×108 EVs/mL are shown in FIGS. 7D and 7E. Western blot and ELISA are the two predominant bulk immunoassays for protein analysis of EVs. In general, LOD of western blot and ELISA are 1012 and 1010 EVs/mL, respectively. There have been efforts to develop highly sensitive techniques which could compete with ELISA for EV protein quantification for medical diagnostic applications. Shao et al. labeled EVs with target-specific magnetic NPs and detected them using a miniaturized micronuclear magnetic resonance (NMR) system. They successfully distinguished glioblastoma multiforme (GBM) derived EVs from host cell-derived EVs based on a four-GBM marker combination (EGFR, EGFRvIII, PDPN and IDH1 R132H). Using CD63-tagged EVs, they claimed that μNMR was 103-fold more sensitive than ELISA. In another study, Im et al. reported a nano-plasmonic exosome (nPLEX) assay based on transmission surface plasmon resonance through periodic nanohole arrays for label-free detection of exosomes. Using this approach, they could identify exosomes from ovarian cancer patients by their expression of CD24 and EpCAM. By measuring CD63 signal, they stated a detection sensitivity of 102-fold higher than that of chemiluminescence ELISA. Although these techniques were demonstrated to be highly sensitive for EV protein quantification, their analytical sensitivities were only examined based on signal intensity of CD63—an abundant biomarker. A validation with PD-L1 is necessary for these techniques to be considered as a diagnostic tool for immunotherapy. For PD-L1 characterization of EVs, in addition to traditional methods—western blot and ELISA, a recent study used flow cytometry to analyze EVs captured on magnetic beads, but its sensitivity was only comparable to western blot21. Lee et al. tried to capture Gli36-WT EVs on a glass slide and perform immunofluorescence staining in order to characterize conventional EV markers (tetraspanins; CD9, CD63, CD81) and tumor markers (EGFR, EGFRvIII, IDH1, IDH1R132, PDPN, PDGFRα, PD-L1, PD-L2), but failed to detect PD-L1 signal. It might be due to the low SNR of their platform, which used glass—a high background substrate. As a result, there has been intense interest in developing a highly sensitive technique for quantification of extracellular vesicular PD-L1 protein for cancer immunotherapy.

Figure 8A:
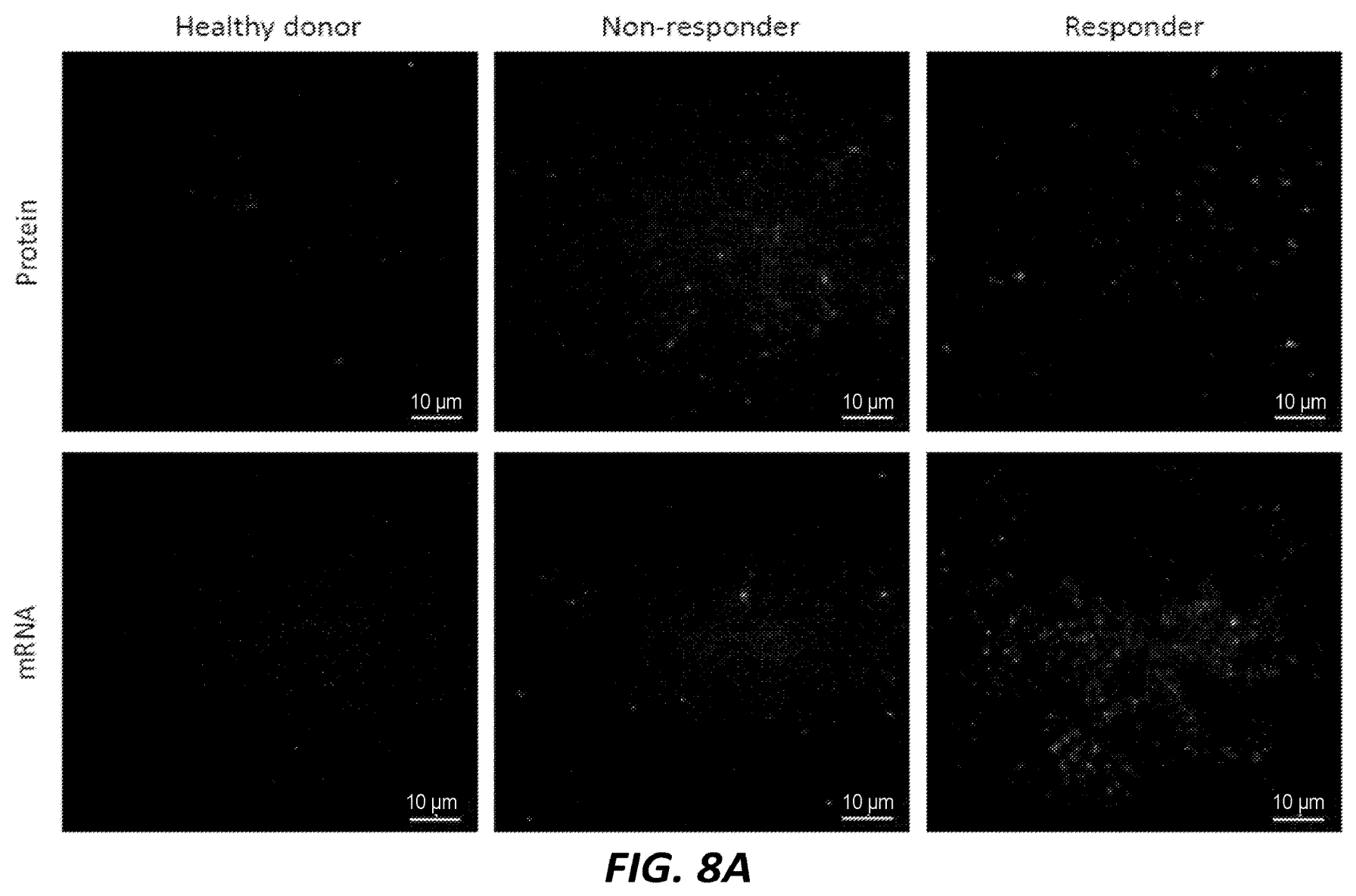
Figure 8B:
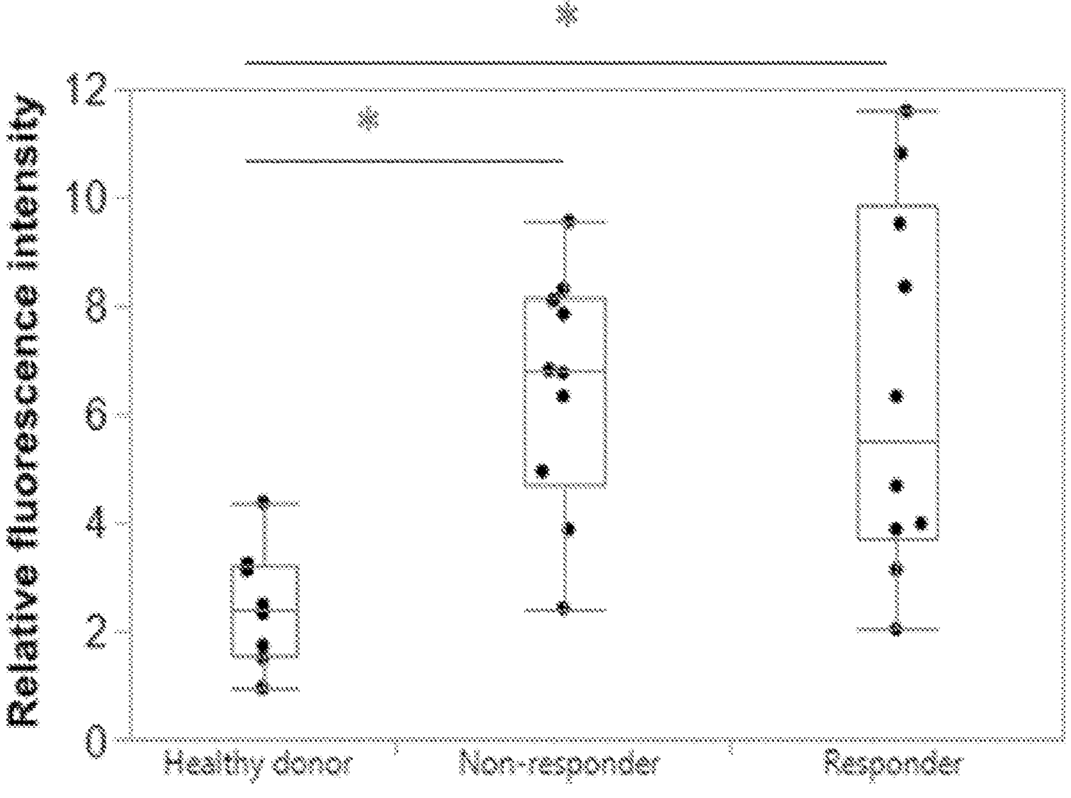
FIG. 8B is a graph of relative fluorescence intensity for the protein captured by the nanogold biochip for non-responders, responders, and healthy donors.
Figure 8C:
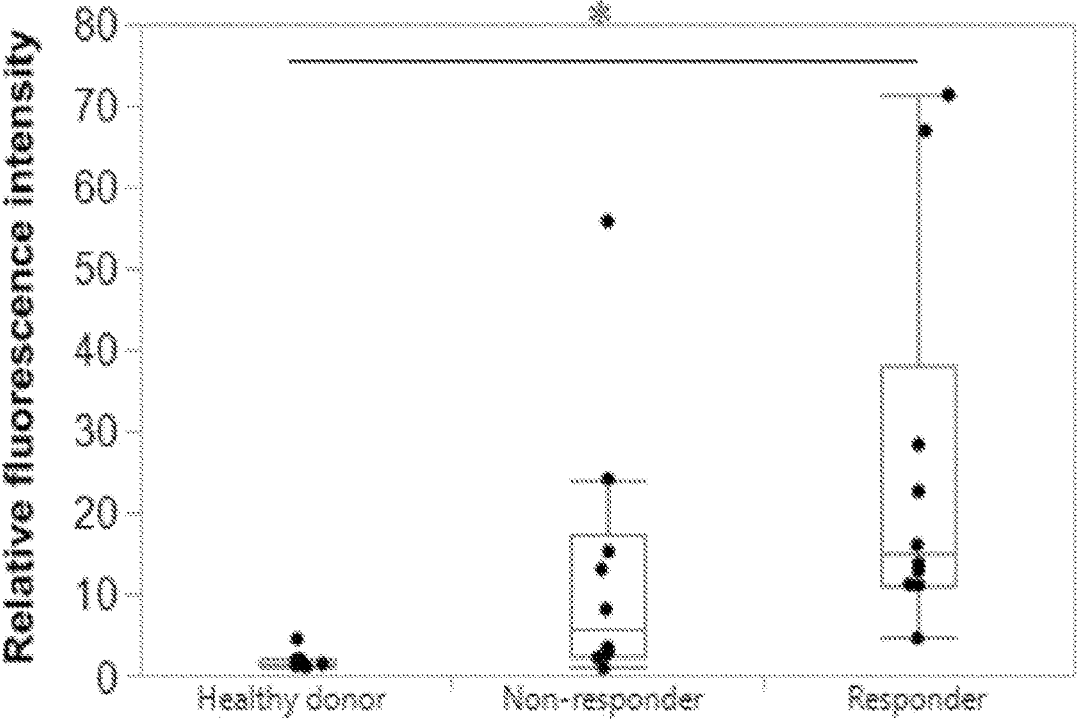
FIG. 8C is a graph of relative fluorescence intensity for the mRNA captured by the nanogold biochip for non-responders, responders, and healthy donors.
Figure 9:
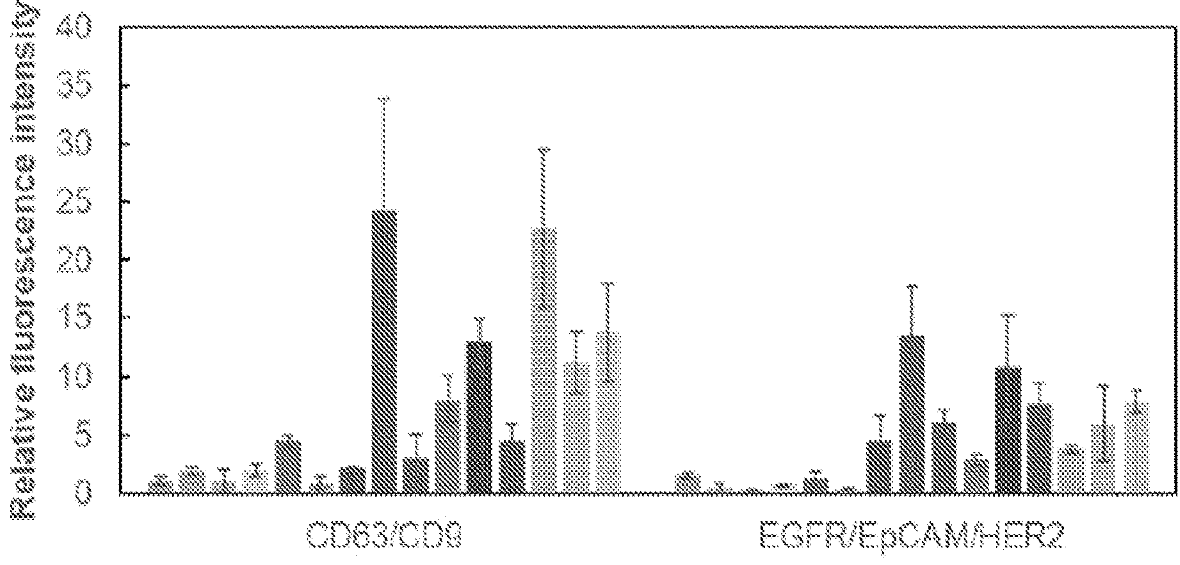
FIG. 9 is a graph of relative fluorescence intensity of PD-L1 mRNA captured by the nanogold biochip for a plurality of different patients and healthy donors using different capture antibodies.
Figure 10:
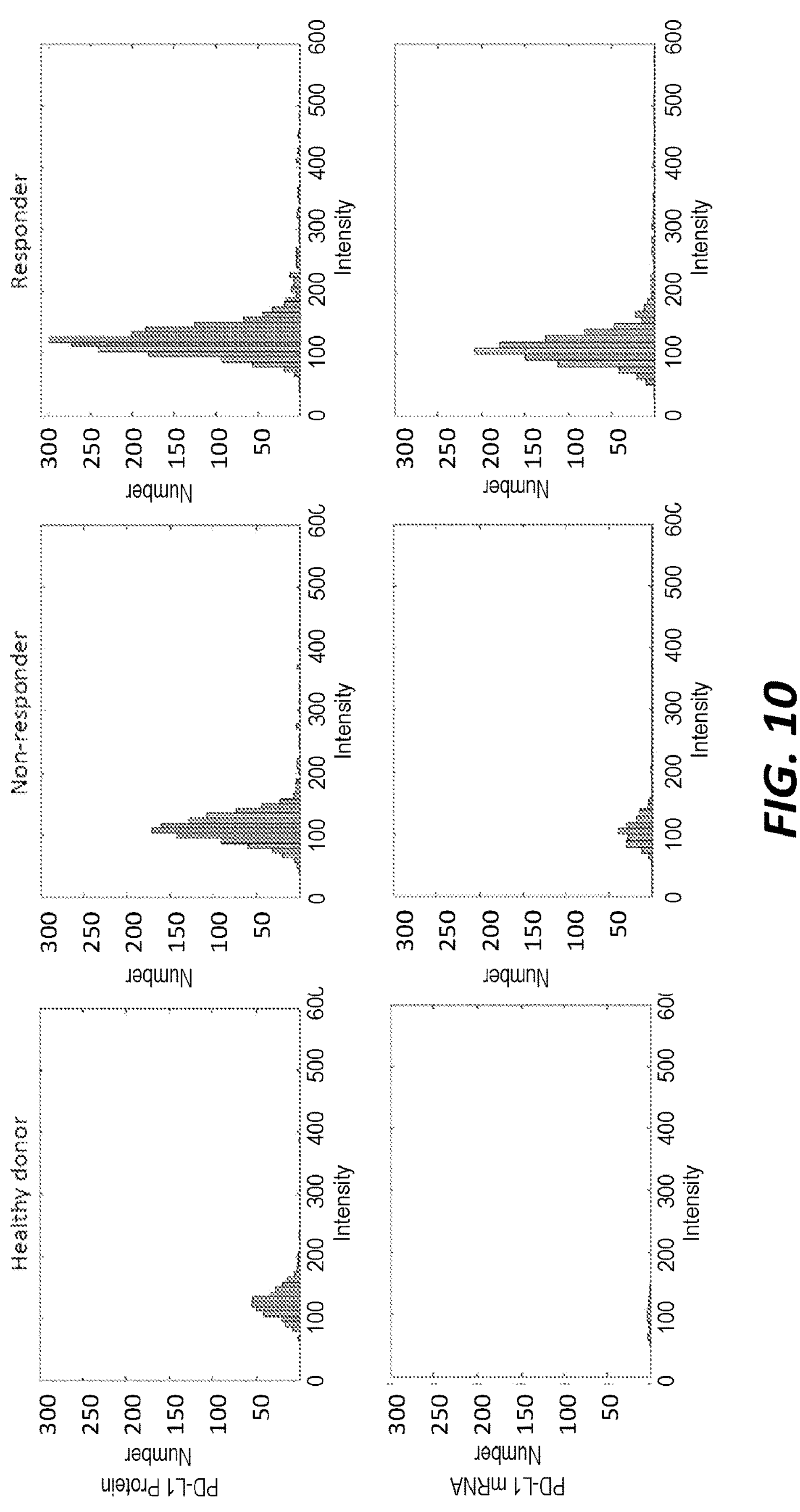
FIG. 10 is a sequence of intensity histograms for PD-L1 protein and PD-L1 mRNA captured by the nanogold biochip for healthy donors, non-responders, and responders.

Quantification of Pd-1/Pd-L1 Proteins and mRNAs from EVs of NSCLC Cancer Patients Treated with Immunotherapy A cohort of 10 non-responders and 10 responders to immunotherapy was chosen for characterization of PD-1/PD-L1 proteins and mRNAs. Our results show that PD-L1 protein and mRNA in EVs of those patients were successfully detected using our biochip platform (FIG. 8A). The PD-L1 protein levels in patient samples (both non-responders and non-responders) were significantly higher than that of healthy donors ($p<0.05$, FIG. 8B). For PD-L1 mRNA levels, there was a significant difference between responders and healthy donors ($p<0.05$, FIG. 8C), but no significant difference between non-responders and healthy donors. In both cases, responders were well-differentiated from healthy donors, but not from non-responders. For PD-L1 protein characterization, a cocktail of EGFR, EpCAM and HER2 was selected as capture antibodies to precisely capture tumor-related EVs for further analysis because PD-L1 is known to be highly expressed in tumor cells. For characterization of PD-L1 mRNA, two different cocktails including CD63/CD9 and EGFR/EpCAM/HER2 were firstly evaluated using a cohort of 5 non-responders and 5 responders (FIG. 9). The bars in the graph of FIG. 9 represent the following patients ordered left to right and then repeated for both CD63/CD9 and EGFR/EpCAM/H1ER2: "Healthy D1," "Healthy D4," "Healthy D6," "Healthy D7," "Healthy D8," "Patient N14," "Patient N25," "Patient N43," "Patient N49," "Patient N67," "Patient R11," "Patient R13," "Patient R45," "Patient R52," and "Patient R53." CD63 and CD9 are abundant tetraspanin surface antigens of exosomes. CD63/CD9 capture was shown to have higher PD-L1 mRNA signals than EGFR/EpCAM/HER2 capture, therefore the CD63/CD9 cocktail was used for the whole cohort of 10 non-responders and 10 responders. Representative histograms of PD-L1 protein/mRNA signals from healthy donors, non-responders and responders are presented in FIG. 10.

Figure 11:
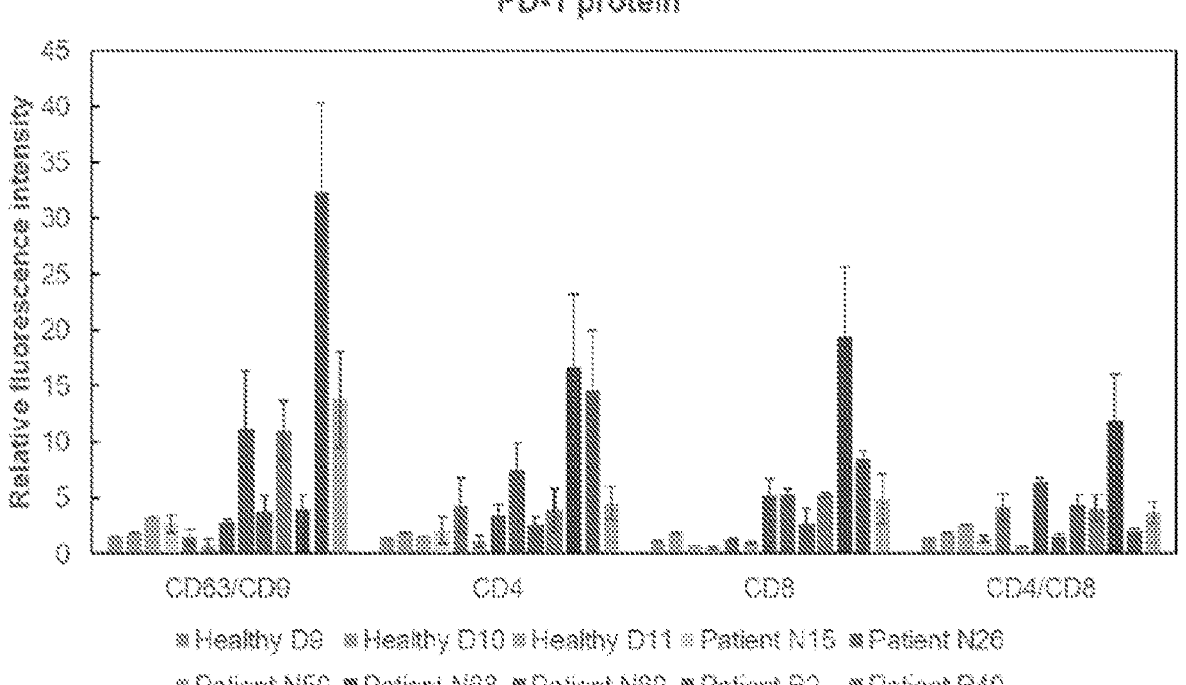
FIG. 11 is a graph of relative fluorescence intensity of PD-L1 protein captured by the nanogold biochip for a plurality of different patients and healthy donors using different capture antibodies.
Figure 12A:
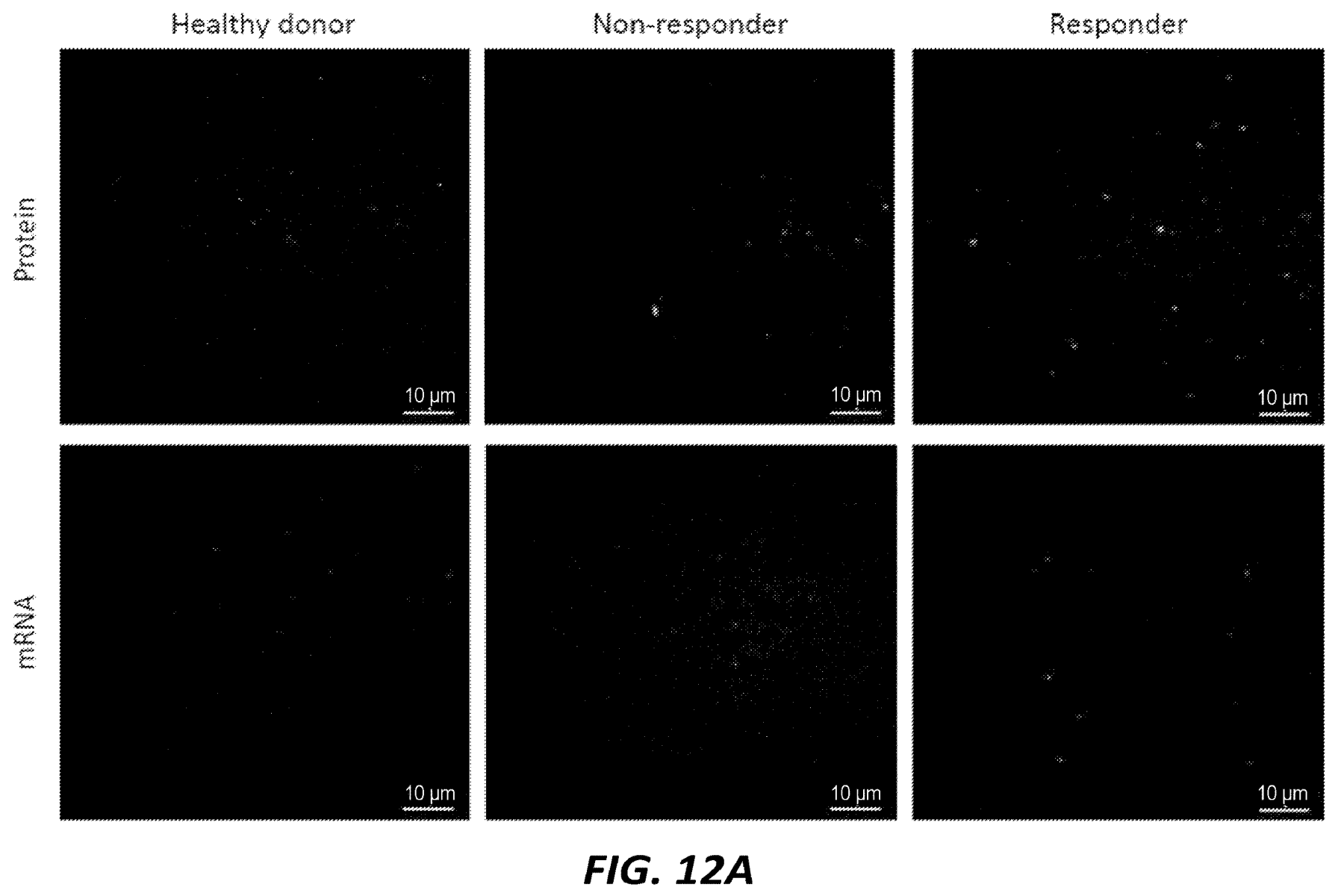
Figure 12B:
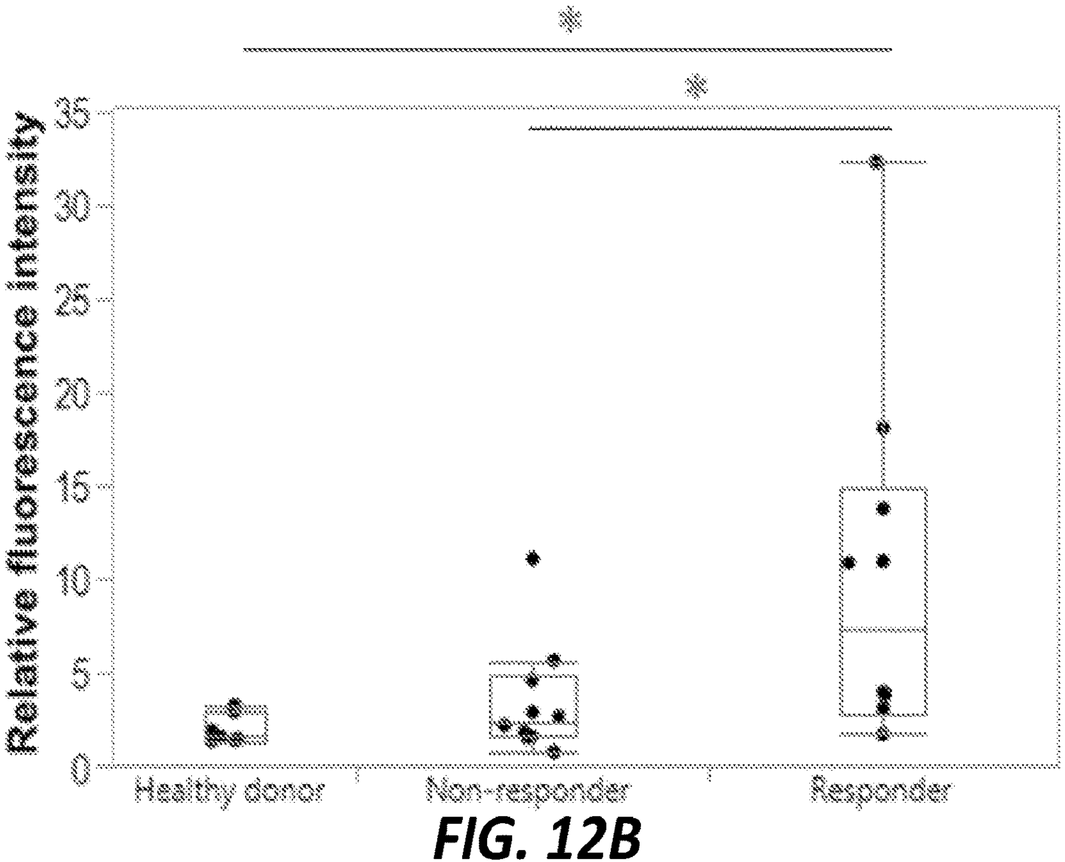
FIG. 12B is a graph of relative fluorescence intensity of PD-L1 protein captured by the nanogold biochip using CD63/CD9 as the capture antibodies for healthy donors, non-responders, and responders.
Figure 12C:
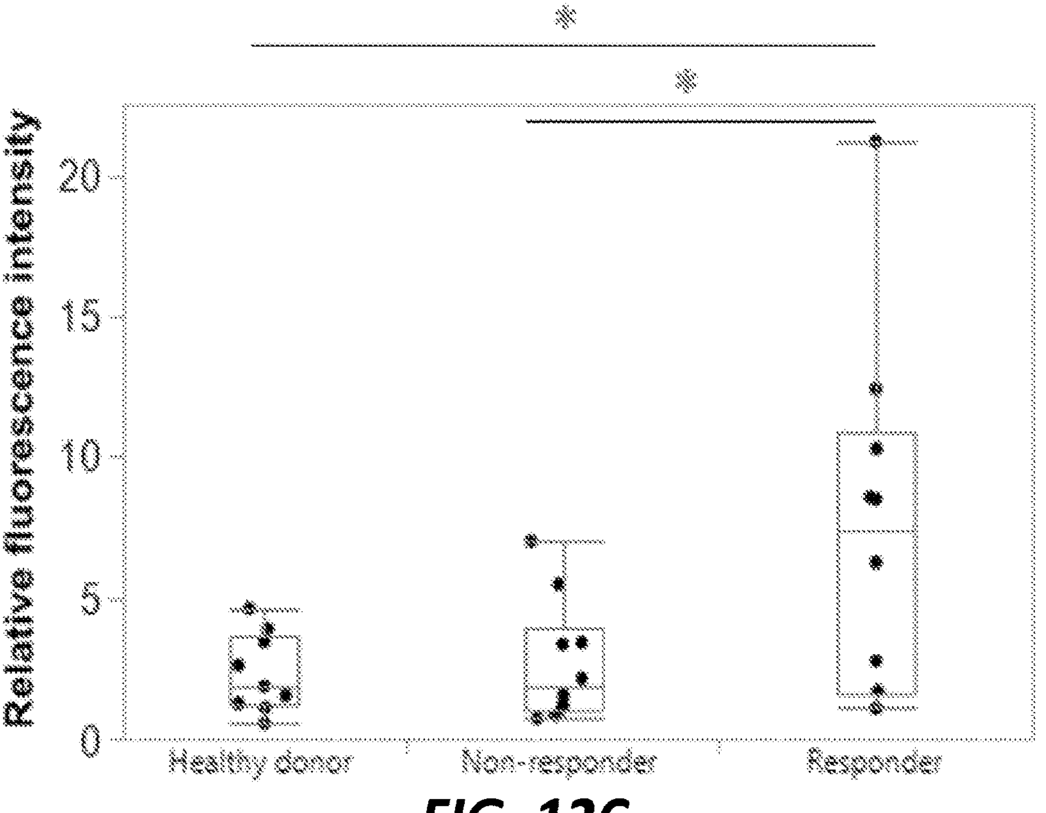
FIG. 12C is a graph of relative fluorescence intensity of PD-L1 mRNA captured by the nanogold biochip using CD63/CD9 as the capture antibodies for healthy donors, non-responders, and responders.
Figure 13:
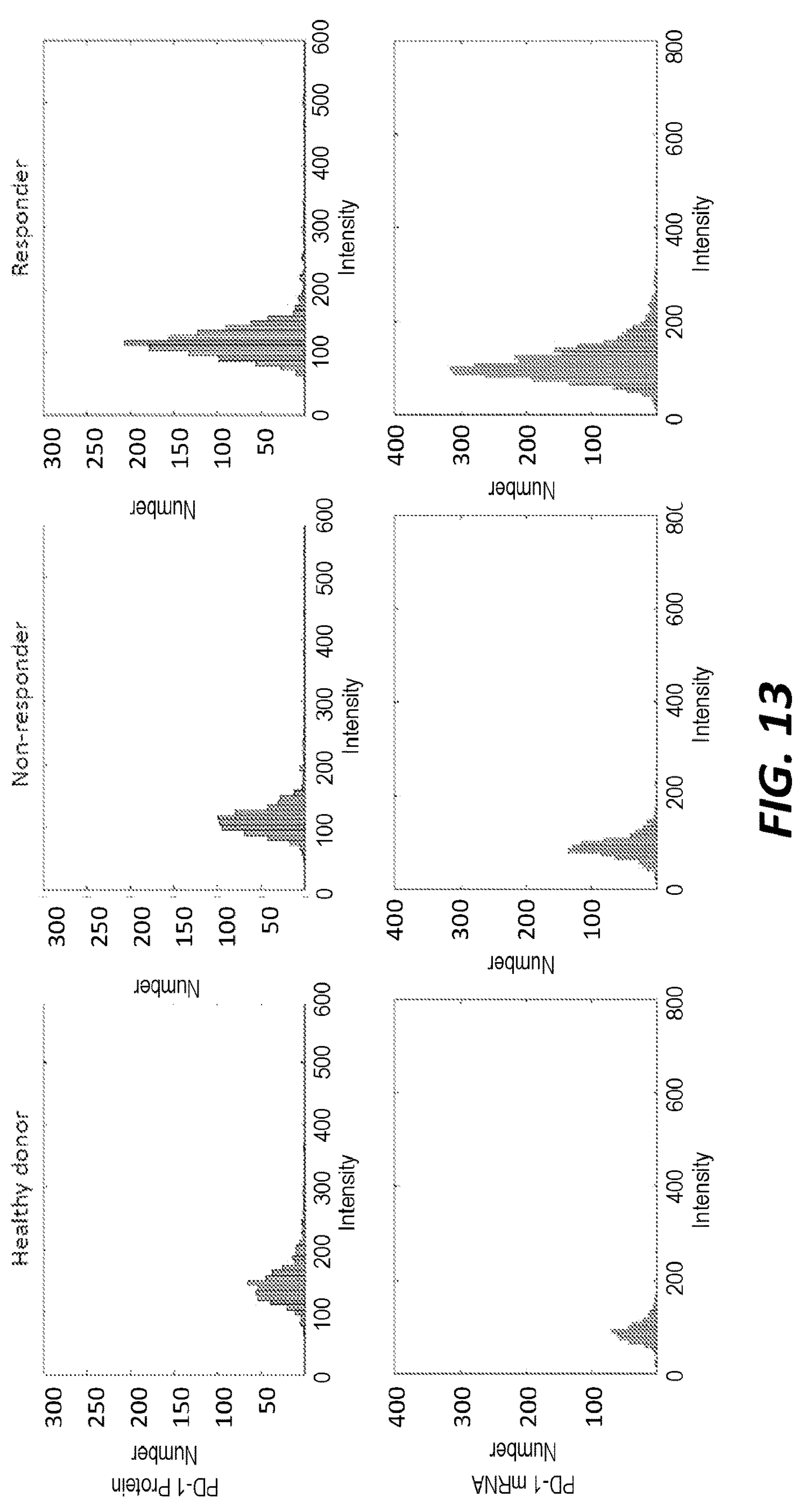
FIG. 13 is a sequence of intensity histograms for the TIRF images of FIG. 12A.

To characterize PD-1 protein in EVs, four different capture antibody cocktails, including CD63/CD9, CD4, CD8 and CD4/CD8 were firstly examined using a cohort of 5 non-responders and 5 responders (FIG. 11). Note that the bars in the graph of FIG. 11 represent the following patients ordered left to right and then repeated for CD63/CD9, CD4, CD8, and CD4/CD8: "Healthy D9," "Healthy D10," "Healthy D11," "Patient N15," "Patient N26," "Patient N50," "Patient N68," "Patient N69," "Patient R2," "Patient R40," "Patient R55," "Patient R62," and "Patient R70." With the highest PD-1 protein signals detected on our platform, CD63/CD9 was selected as the capture cocktail for the whole cohort. In contrast to PD-L1 protein/mRNA signals, PD-1 protein levels in responders were significantly higher than both non-responders and healthy donors ($p<0.05$, FIG. 12A). Similar findings were observed for PD-1 mRNA with CD63/CD9 as capture antibodies ($p<0.05$, FIGS. 12B and 12C). Representative histograms of PD-1 protein/mRNA signals from different samples are shown in FIG. 13.

Figures 14A, 14B:
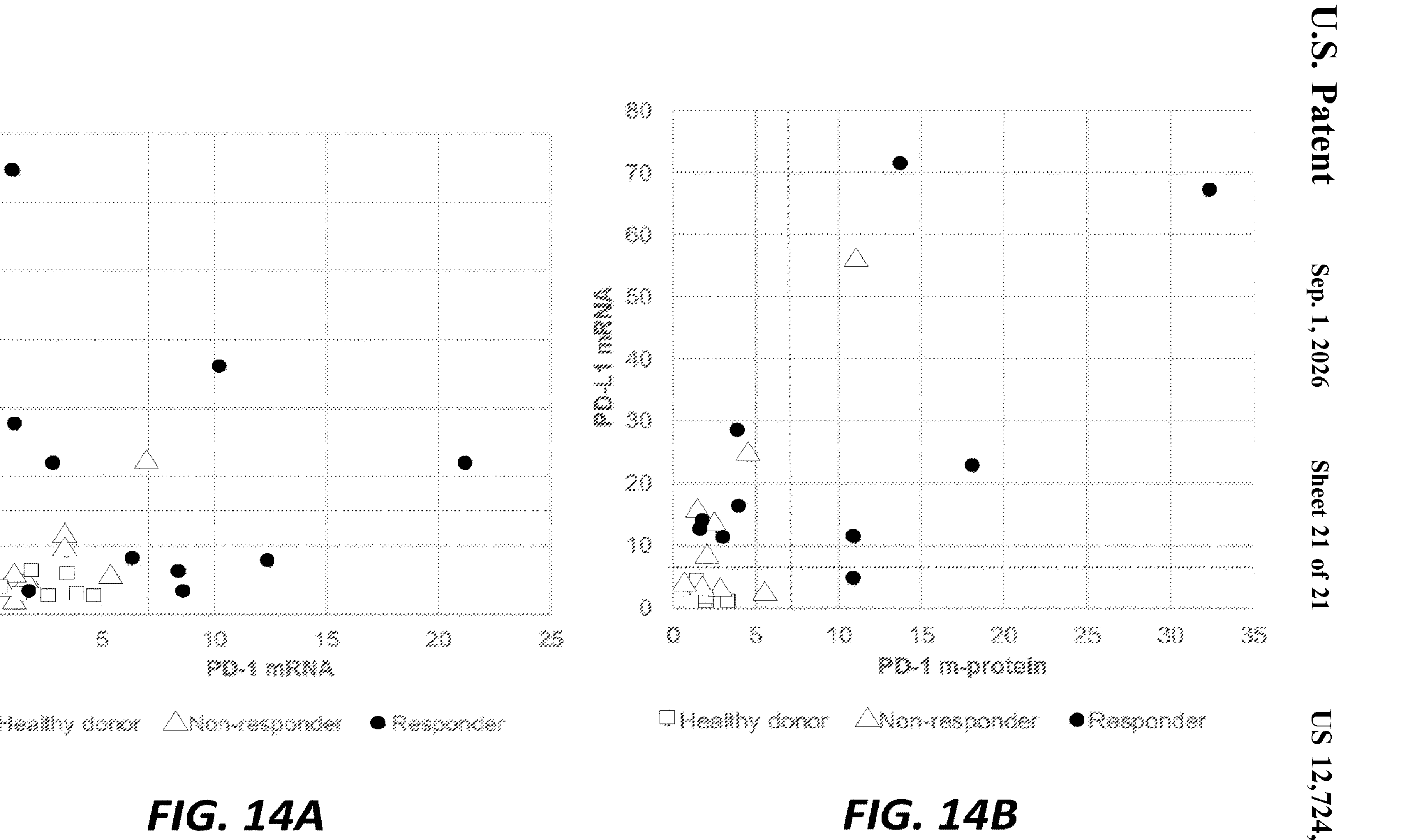
FIG. 14A is a scatter plot graph of PD-1 mRNA expression level vs. PD-1 m-protein expression level for each plurality of non-responders, responders, and healthy donors.
FIG. 14B is a scatter plot graph of PD-L1 mRNA expression level vs. PD-1 m-protein expression level for each plurality of non-responders, responders, and healthy donors.

Taken together, we successfully detected and quantified PD-1/PD-L1 proteins and mRNAs in EVs purified from NSCLC serum samples. With our biochip platform, each biomarker can be accurately measured with ~3 μL serum starting volume. Scatter plots reveal that with a threshold fold change of '7' for both EV mRNA and EV protein expression levels, a dual PD-1 protein/PD-1 mRNA and PD-1 protein/PD-L1 mRNA biomarkers may be helpful for identifying responders from non-responders of NSCLC patients for anti-PD-1/PD-L1 immunotherapy (FIGS. 14A and 14B). Different EV subpopulations (based on different capture antibodies) and/or more biomarkers can be characterized to well-differentiate between responders and non-responders.

Lung cancer is the second most common cancer and the most leading cause of cancer death in both men and women in the U.S., and about 80-85% of lung cancers are NSCLC (Cancer Statistics Center, American Cancer Society, 2019). Till now, FDA has approved three ICIs targeting PD-L1 (atezolizumab, durvalumab and avelumab) and two ICIs targeting PD-1 (nivolumab, pembrolizumab) for NSCLC patients with positive PD-L1 expression; however their objective response rates (ORR) were only less than 20%. This may be because PD-L1 IHC staining of tissue biopsies are not representative enough of the entire tumor burden. EVs, which are shed from primary and metastatic tumors and circulated in the bloodstream, can represent cancer heterogeneity and therefore become an ideal source for the quantification of immunotherapy biomarkers. Previous studies have shown that PD-L1 proteins are present on the surface of EVs isolated from plasma/serum of patients with metastatic melanomas, head and neck squamous cell carcinomas, gliomas, and NSCLC. In addition to PD-L1 proteins, PD-L1 mRNAs have been demonstrated to exist in EVs derived from saliva and plasma of patients with periodontitis and melanoma/NSCLC, respectively. Compared to PD-L1 proteins/mRNAs, studies on PD-1 biomarkers in EVs are limited, with only one showing the presence of PD-1 proteins on the surface of EVs. The majority of these studies used western blot, magnetic bead-based flow cytometry, RT-PCR and ddPCR to measure EV protein and mRNA levels in bulk with limited sensitivity. In this study, we therefore aimed to develop a highly sensitive technology to quantify molecular contents in EVs at the single level and simultaneously measure protein and mRNA contents on the same device.

Our biochip platform was successfully made with significantly high SNR of 482.02±21.81, which enabled us to accurately quantify low expression biomarkers of PD-1/PD-L1 proteins/mRNAs. Our platform revealed ~100 times more sensitive than ELISA in quantification of PD-L1 protein. With such high sensitivity, our technology only required ~3 μL serum starting volume for each biomarker measurement. Recently, Pang et al. claimed that with Fe3O4@TiO2 isolation and Surface-Enhanced Raman Scattering (SERS) immunoassay, they could quantify EV PD-L1 protein from 4 μL clinical serum sample and NSCLC patients could be distinguished from the healthy controls based on their PD-L1 protein expression levels. SERS has been known as an ultrasensitive analytical technique with multiplexing capability and single-molecule measurement; however, it suffers from significantly longer acquisition time than fluorescence imaging.

We successfully demonstrated a comprehensive profile of four immunotherapy biomarkers, PD-1/PD-L1 proteins on the surface and PD-1/PD-L1 mRNAs in the serum-derived EVs, of NSCLC patients. A cohort of 10 non-responders and 10 responders was examined in our study. While PD-L1 protein/mRNA levels of responders were only significantly higher than healthy donors, PD-1 protein/mRNA levels responders were shown to be significant different from both non-responders and healthy donors. The combination of dual PD-1 protein and mRNA biomarkers could therefore well-differentiate between responders and non-responders. Further investigations using larger cohorts will be performed to validate findings in the current studies. We believe that our platform has a strong potential to be developed as minimally invasive diagnostics and monitoring tool for cancer. The success of this work is a breakthrough in cancer therapy in which personalized cancer immunotherapy can be achieved by feasibly identifying patients most likely to benefit from immunotherapy and monitoring the response throughout the course of treatment.

Thus, the invention provides, among other things, a biochip for characterization of extracellular vesicular biomarkers including gold nanoparticles, methods of manufacturing the gold nanoparticle biochip, and methods for analyzing EV biomarkers using the gold nanoparticle biochip. Other features and advantages of the invention are set forth in the accompanying claims and the attached appendix.

What is claimed is:

1. A biochip for characterization of extracellular vesicular biomarkers for cancer immunotherapy, the biochip comprising:

a glass surface;

a gold film layer on the glass surface;

a plurality of gold nanoparticles coupled to the gold film layer; and a plurality of biotinylated antibodies coupled to the gold nanoparticles, wherein the biotinylated antibodies are selected to capture extracellular vesicles, wherein the biotinylated antibodies comprise antibodies against CD63 and CD9; and wherein the gold film layer is coated with a linker that is biotin-polyethylene glycol-thiol (biotin-PEG-SH) and the plurality of gold nanoparticles are a plurality of streptavidin-conjugated gold nanoparticles, such that the plurality of streptavidin-conjugated gold nanoparticles are coupled to the gold film layer by the linker.

2. The biochip of claim 1, wherein the gold film layer coated with the linker is formed by exposing the surface to a linker solution comprising the linker, and wherein the linker solution further includes at least one selected from a group consisting of a 1-thiahexa(ethyleneoxide) lipidic anchor molecule 20-tetradecyloxy-3,6,7,12,15,18,22-heptaoxahexa-tricontane-1-thioil (WC14), and a lateral spacer β-mercaptoethanol.

3. The biochip of claim 1, wherein the gold film layer is coupled to the glass surface by a layer of (3-mercaptopropyl) trimethoxysilane (MPTMS).

4. The biochip of claim 1, wherein each gold nanoparticle of the plurality of gold nanoparticles has a diameter of 30 nanometers.

5. An assay platform system for identifying candidates for cancer immunotherapy, the system comprising:

the biochip of claim 1; and a total internal reflection fluorescence (TIRF) microscope imaging system configured to capture image data of extracellular vesicular biomarker captured by the biochip.

6. A method of characterizing extracellular vesicular biomarkers for cancer immunotherapy, the method comprising:

applying purified extracellular vesicles from a biofluid of a first patient to the biochip of claim 1;

washing the biochip with phosphate-buffered saline (PBS) solution;

applying a plurality of molecular beacons to the washed biochip;

washing the biochip with PBS solution;

capturing image data of the biochip with a total internal reflection fluorescence (TIRF) microscope; and detecting and quantifying the EV biomarker based on the captured image data.

7. The method of claim 6, wherein applying the plurality of molecular beacons to the washed biochip includes applying a plurality of cationic lipoplex nanoparticles (CLN) containing PD-1/PD-L1 target-specific molecular beacons.

8. The method of claim 6, further comprising:

comparing the determined quantity of the extracellular vesicular biomarker to a threshold value; and determining whether the first patient is a candidate for cancer immunotherapy based at least in part on the comparison of the determined quantity of the extracellular vesicular biomarker and the threshold value.

* * * * *